(12) United States Patent
Saha

(10) Patent No.: US 8,137,933 B2
(45) Date of Patent: Mar. 20, 2012

(54) MAMMALIAN EXPRESSION VECTOR PUHAB

(75) Inventor: Deba P. Saha, Nutley, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/617,497

(22) Filed: Nov. 12, 2009

(65) Prior Publication Data
US 2010/0120090 A1    May 13, 2010

Related U.S. Application Data

(60) Provisional application No. 61/113,824, filed on Nov. 12, 2008.

(51) Int. Cl.
*C12P 21/00* (2006.01)
*C12N 15/63* (2006.01)
*C07K 16/00* (2006.01)

(52) U.S. Cl. .................. 435/70.1; 435/320.1; 530/387.1

(58) Field of Classification Search ........................ None
See application file for complete search history.

(56) References Cited

U.S. PATENT DOCUMENTS

| | | | |
|---|---|---|---|
| 7,217,796 B2 | 5/2007 | Wang et al. | |
| 7,326,567 B2 | 2/2008 | Saha | |

FOREIGN PATENT DOCUMENTS

| | | |
|---|---|---|
| WO | WO91/13160 | 9/1991 |
| WO | WO01/88121 | 11/2001 |
| WO | WO02/14525 | 2/2002 |
| WO | WO2010/056816 | 5/2010 |

OTHER PUBLICATIONS

Norderhaug L, Olafsen T, Michaelsen TE, Sandlie I.Versatile vectors for transient and stable expression of recombinant antibody molecules in mammalian cells. J Immunol Methods. May 12, 1997; 204(1):77-87.

Zhang R, DeGroot LJ. An adenoviral vector expressing functional heterogeneous proteins herpes simplex viral thymidine kinase and human interleukin-2 has enhanced in vivo antitumor activity against medullary thyroid carcinoma. Endocr Relat Cancer. Dec. 2001;8 (4) :315-25.

Flamez D, Remaut E, Fiers W. Production in *Escherichia coli* of a functional murine and murine::human chimeric F(ab')2 fragment and mature antibody directed against human placental alkaline phosphatase. J Biotechnol. Sep. 29, 1995;42(2):133-43.

Bebbington C.R. Expression of antibody genes in nonlymphoid mammalian cells. Methods: A companion to Methods in Enzymology. Academic Press, Inc. New York, NY 2(2): 136-145 (1991).

Page MJ, Sydenham MA. High level expression of the humanized monoclonal antibody Campath-1H in Chinese hamster ovary cells. Biotechnology (N Y). Jan. 1991;9(1):64-8.

Wahle E The end of the message: 3' -end processing leading to polyadenylated messenger RNA. Bioessays. Feb. 1992;14(2):113-8.

Oberholzer A, Oberholzer C, Bahjat KS, Ungaro R, Tannahill CL, Murday M, Bahjat FR, Abouhamze Z, Tsai V, LaFace D, Hutchins B, Moldawer LL, Clare-Salzler MJ. Increased survival in sepsis by in vivo adenovirus-induced expression of IL-10 in dendritic cells. J Immunol. Apr. 1, 2002;168(7) :3412-8.

Takebe Y, Seiki M, Fujisawa J, Hoy P, Yokota K, Arai K, Yoshida M, Arai N. SR alpha promoter: an efficient and versatile mammalian cDNA expression system composed of the simian virus 40 early promoter and the R-U5 segment of human T-cell leukemia virus type 1 long terminal repeat. Mol Cell Biol. Jan. 1988;8(1):466-72.

Ju G, Skalka AM. Nucleotide sequence analysis of the long terminal repeat (LTR) of avian retroviruses: structural similarities with transposable elements. Cell. Nov. 1980;22(2 Pt 2) :379-86.

Kaufman. Selection and Coamplification of Heterologous Genes in Mammalian Cells. Methods in Enzymology 185: 537-566 (1990).

Green LL. Antibody engineering via genetic engineering of the mouse: XenoMouse strains are a vehicle for the facile generation of therapeutic human monoclonal antibodies. J Immunol Methods. Dec. 10, 1999;231(1-2):11-23.

*Primary Examiner* — Celine Qian

(57) ABSTRACT

The present invention relates to the construction and utilization of a new mammalian expression vector that contains a unique multiple cloning site (MCS), designated pUHAB. The pUHAB vector comprises a high copy replication origin (ColE1), a drug resistance gene (TK-Hygromycin), and a human cytomegalovirus promoter operably associated with a unique intron (hCMV/intron). Further, pUHAB comprises a selectable marker conferring resistance to kanamycin in bacterial cells, and a phage f1(+) region. pUHAB can be used to transiently or stably express cloned genes when transfected into mammalian cells. The invention also encompasses kits and host cells and cell lines comprising pUHAB, and methods of producing a recombinant protein using pUHAB.

4 Claims, 8 Drawing Sheets

Figure 1: pUHAB Sequence (a)

BamHI
~~~~~

```
   1    GCTGGATCCA GATCCCCCTC GCTTTCTTGC TGTCCAATTT CTATTAAAGG TTCCTTTGTT
  61    CCCTAAGTCC AACTACTAAA CTGGGGGATA TTATGAAGGG CCTTGAGCAT CTGGATTCTG
 121    CCTAATAAAA AACATTTATT TTCATTGCAA TGATGTATTT AAATTATTTC TGAATATTTT
 181    ACTAAAAAGG GAATGTGGGA GGTCAGTGCA TTTAAAACAT AAAGAAATGA AGAGGGGGAT
 241    CTGTCGACAA GCTCTAGAGA GCTCACGCGT TGATCATGTA CAGGCCGGCC AAGCTTTCGA
 301    CTAGCTTGGC ACGCCAGAAA TCCGCGCGGT GGTTTTTGGG GGTCGGGGGT GTTTGGCAGC
 361    CACAGACGCC CGGTGTTCGT GTCGCGCCAG TACATGCGGT CCATGCCCAG GCCATCCAAA
 421    AACCATGGGT CTGTCTGCTC AGTCCAGTCG TGGACCTGAC CCCACGCAAC GCCCAAAATA
 481    ATAACCCCCA CGAACCATAA ACCATTCCCC ATGGGGGACC CCGTCCCTAA CCCACGGGGC
 541    CAGTGGCTAT GGCAGGCCT GCCGCCCCGA CGTTGGCTGC GAGCCCTGGG CCTTCACCCG
 601    AACTTGGGGG GTGGGGTGGG GAAAAGGAAG AAACGCGGGC GTATTGGCCC CAATGGGGTC
 661    TCGGTGGGTG ATCGACAGAG TGCCAGCCCT GGGACCGAAC CCCGCGTTTA TGAACAAACG
 721    ACCCAACACC CGTGCGTTTT ATTCTGTCTT TTTATTGCCG TCATAGCGCG GGTTCCTTCC
 781    GGTATTGTCT CCTTCCGTGT TTCAGTTAGC CTCCCCCATC TCCCGATCCG GACGAGTGCT
 841    GGGGCGTCGG TTTCCACTAT CGGCGAGTAC TTCTACACAG CCATCGGTCC AGACGGCCGC
 901    GCTTCTGCGG GCGATTTGTG TACGCCCGAC AGTCCCGGCT CCGGATCGGA CGATTGCGTC
 961    GCATCGACCC TGCGCCCAAG CTGCATCATC GAAATTGCCG TCAACCAAGC TCTGATAGAG
1021    TTGGTCAAGA CCAATGCGGA GCATATACGC CCGGAGCCGC GGCGATCCTG CAAGCTCCGG
1081    ATGCCTCCGC TCGAAGTAGC GCGTCTGCTG CTCCATACAA GCCAACCACG GCCTCCAGAA
1141    GAAGATGTTG GCGACCTCGT ATTGGGAATC CCCGAACATC GCCTCGCTCC AGTCAATGAC
1201    CGCTGTTATG CGGCCATTGT CCGTCAGGAC ATTGTTGGAG CCGAAATCCG CGTGACGAG
1261    GTGCCGGACT TCGGGGCAGT CCTCGGCCCA AAGCATCAGC TCATCGAGAG CCTGCCCGAC
1321    GGACGCACTG ACGGTGTCGT CCATCACAGT TTGCCAGTGA TACACATGGG GATCAGCAAT
1381    CGCGCATATG AAATCACGCC ATGTAGTGTA TTGACCGATT CCTTGCGGTC CGAATGGGCC
1441    GAACCCGCTC GTCTGGCTAA GATCGGCCGC AGCGATCGCA TCCATGGCCT CCGCGACCGG
1501    CTGCAGAACA GCGGGCAGTT CGGTTTCAGG CAGGTCTTGC AACGTGACAC CCTGTGCACG
1561    GCGGGAGATG CAATAGGTCA GGCTCTCGCT GAATTCCCCA ATGTCAAGCA CTTCCGGAAT
1621    CGGGAGCGCG GCCGATGCAA AGTGCCGATA AACATAACGA TCTTTGTAGA AACCATCGGC
1681    GCAGCTATTT ACCCGCAGGA CATATCCACG CCCTCCTACA TCGAAGCTGA AAGCACGAGA
1741    TTCTTCGCCC TCCGAGAGCT GCATCAGGTC GGAGACGCTG TCGAACTTTT CGATCAGAAA
1801    CTTCTCGACA GACGTCGCGG TGAGTTCAGG CTTTTTCATA TCTCATTGCC CCCGGGATC
1861    TGCGGCACGC TGTTGACGCT GTTAAGCGGG TCGCTGCAGG GTCGCTCGGT GTTCGAGGCC
1921    ACACGCGTCA CCTTAATATG CGAAGTGGAC CTCGGACCGC GCCGCCCCGA CTGCATCTGC
1981    GTGTTCGAAT TCGCCAATGA CAAGACGCTG GGCGGGGTTT GTGTCATCAT AGAACTAAAG
2041    ACATGCAAAT ATATTTCTTC CGGGGACACC GCCAGCAAAC GCGAGCAACG GGCCACGGGG
2101    ATGAAGCAGG GCGGCACCTC GCTAACGGAT TCACCACTCC AAGAATTGGA GCCAATCAAT
2161    TCTTGCGGAG AACTGTGAAT GCGCAAACCA ACCCTTGGCA GAACATATCC ATCGCGTCCG
2221    CCATCTCCAG CAGCCGCACG CGGCGCATCT CGGGGCCGAC GCGCTGGGCT ACGTCTTGCT
2281    GGCGTTCGCA CAGGCCGGCC AGCGCGCTCA CTGGCCGTCG TTTTACAACG TCGTGACTGG
2341    GAAAACCCTG GCGTTACCCA ACTTAATCGC CTTGCAGCAC ATCCCCCTTT CGCCAGCTGG
2401    CGTAATAGCG AAGAGGCCCG CACCGATCGC CCTTCCCAAC AGTTGCGCAG CCTGAATGGC
2461    GAATGGGACG CGCCCTGTAG CGGCGCATTA AGCGCGGCGG GTGTGGTGGT TACGCGCAGC
2521    GTGACCGCTA CACTTGCCAG CGCCCTAGCG CCCGCTCCTT TCGCTTTCTT CCCTTCCTTT
2581    CTCGCCACGT TCGCCGGCTT TCCCCGTCAA GCTCTAAATC GGGGGCTCCC TTTAGGGTTC
2641    CGATTTAGTG CTTTACGGCA CCTCGACCCC AAAAAACTTG ATTAGGGTGA TGGTTCACGT
2701    AGTGGGCCAT CGCCCTGATA GACGGTTTTT CGCCCTTTGA CGTTGGAGTC CACGTTCTTT
2761    AATAGTGGAC TCTTGTTCCA AACTGGAACA ACACTCAACC CTATCTCGGT CTATTCTTTT
2821    GATTTATAAG GGATTTTGCC GATTTCGGCC TATTGGTTAA AAAATGAGCT GATTTAACAA

2881    AAATTTAACG CGAATTTTAA CAAAATATTA ACGCTTACAA TTTAGGTGGC ACTTTTCGGG
2941    GAAATGTGCG CGGAACCCCT ATTTGTTTAT TTTTCTAAAT ACATTCAAAT ATGTATCCGC
3001    TCATGAGACA ATAACCCTGA TAAATGCTTC AATAATATTG AAAAAGGAAG AGTATGAGTA
```

Figure 1 (cont)

(b)
```
3061    TTCAACATTT CCGTGTCGCC CTTATTCCCT TTTTTGCGGC ATTTTGCCTT CCTGTTTTTG
3121    CTCACCCAGA AACGCTGGTG AAAGTAAAAG ATGCTGAAGA TCAGTTGGGT GCACGAGTGG
3181    GTTACATCGA ACTGGATCTC AACAGCGGTA AGATCCTTGA GAGTTTTCGC CCCGAAGAAC
3241    GCCTGAATCG CCCCATCATC CAGCCAGAAA GTGAGGGAGC CACGGTTGAT GAGAGCTTTG
3301    TTGTAGGTGG ACCAGTTGGT GATTTTGAAC TTTTGCTTTG CCACGGAACG GTCTGCGTTG
3361    TCGGGAAGAT GCGTGATCTG ATCCTTCAAC TCAGCAAAAG TTCGATTTAT TCAACAAAGC
3421    CACGTTGTGT CTCAAAATCT CTGATGTTAC ATTGCACAAG ATAAAAATAT ATCATCATGA
3481    ACAATAAAAC TGTCTGCTTA CATAAACAGT AATACAAGGG GTGTTATGAG CCATATTCAA
3541    CGGGAAACGT CTTGCTCGAG GCCGCGATTA AATTCCAACA TGGATGCTGA TTTATATGGG
3601    TATAAATGGG CTCGCGATAA TGTCGGGCAA TCAGGTGCGA CAATCTATCG ATTGTATGGG
3661    AAGCCCGATG CGCCAGAGTT GTTTCTGAAA CATGGCAAAG GTAGCGTTGC CAATGATGTT
3721    ACAGATGAGA TGGTCAGACT AAACTGGCTG ACGGAATTTA TGCCTCTTCC GACCATCAAG
3781    CATTTTATCC GTACTCCTGA TGATGCATGG TTACTCACCA CTGCGATCCC CGGGAAAACA
3841    GCATTCCAGG TATTAGAAGA ATATCCTGAT TCAGGTGAAA ATATTGTTGA TGCGCTGGCA
3901    GTGTTCCTGC GCCGGTTGCA TTCGATTCCT GTTTGTAATT GTCCTTTTAA CAGCGATCGC
3961    GTATTTCGTC TCGCTCAGGC GCAATCACGA ATGAATAACG GTTTGGTTGA TGCGAGTGAT
4021    TTTGATGACG AGCGTAATGG CTGGCCTGTT GAACAAGTCT GGAAAGAAAT GCATAAGCTT
4081    TTGCCATTCT CACCGGATTC AGTCGTCACT CATGGTGATT TCTCACTTGA TAACCTTATT
4141    TTTGACGAGG GGAAATTAAT AGGTTGTATT GATGTTGGAC GAGTCGGAAT CGCAGACCGA
4201    TACCAGGATC TTGCCATCCT ATGGAACTGC CTCGGTGAGT TTTCTCCTTC ATTACAGAAA
4261    CGGCTTTTTC AAAAATATGG TATTGATAAT CCTGATATGA ATAAATTGCA GTTTCATTTG
4321    ATGCTCGATG AGTTTTTCTA ATCAGAATTG GTTAATTGGT TGTAACACTG GCAGAGCATT
4381    ACGCTGACTT GACGGGACGG CGGCTTTGTT GAATAAATCG AACTTTTGCT GAGTTGAAGG
4441    ATCAGATCAC GCATCTTCCC GACAACGCAG ACCGTTCCGT GGCAAAGCAA AAGTTCAAAA
4501    TCACCAACTG GTCCACCTAC AACAAAGCTC TCATCAACCG TGGCTCCCTC ACTTTCTGGC
4561    TGGATGATGG GGCGATTCAG GCGTTGCGCA AACTATTAAC TGGCGAACTA CTTACTCTAG
4621    CTTCCCGGCA ACAATTAATA GACTGGATGG AGGCGGATAA AGTTGCAGGA CCACTTCTGC
4681    GCTCGGCCCT TCCGGCTGGC TGGTTTATTG CTGATAAATC TGGAGCCGGT GAGCGTGGGT
4741    CTCGCGGTAT CATTGCAGCA CTGGGGCCAG ATGGTAAGCC CTCCCGTATC GTAGTTATCT
4801    ACACGACGGG GAGTCAGGCA ACTATGGATG AACGAAATAG ACAGATCGCT GAGATAGGTG
4861    CCTCACTGAT TAAGCATTGG TAACTGTCAG ACCAAGTTTA CTCATATATA CTTTAGATTG
4921    ATTTAAAACT TCATTTTTAA TTTAAAAGGA TCTAGGTGAA GATCCTTTTT GATAATCTCA
4981    TGACCAAAAT CCCTTAACGT GAGTTTTCGT TCCACTGAGC GTCAGACCCC GTAGAAAAGA
5041    TCAAAGGATC TTCTTGAGAT CCTTTTTTTC TGCGCGTAAT CTGCTGCTTG CAAACAAAAA
5101    AACCACCGCT ACCAGCGGTG GTTTGTTTGC CGGATCAAGA GCTACCAACT CTTTTTCCGA
5161    AGGTAACTGG CTTCAGCAGA GCGCAGATAC CAAATACTGT CCTTCTAGTG TAGCCGTAGT
5221    TAGGCCACCA CTTCAAGAAC TCTGTAGCAC CGCCTACATA CCTCGCTCTG CTAATCCTGT
5281    TACCAGTGGC TGCTGCCAGT GGCGATAAGT CGTGTCTTAC CGGGTTGGAC TCAAGACGAT
5341    AGTTACCGGA TAAGGCGCAG CGGTCGGGCT GAACGGGGGG TTCGTGCACA CAGCCCAGCT
5401    TGGAGCGAAC GACCTACACC GAACTGAGAT ACCTACAGCG TGAGCTATGA GAAAGCGCCA
5461    CGCTTCCCGA AGGGAGAAAG GCGGACAGGT ATCCGGTAAG CGGCAGGGTC GGAACAGGAG
5521    AGCGCACGAG GGAGCTTCCA GGGGGAAACG CCTGGTATCT TTATAGTCCT GTCGGGTTTC
5581    GCCACCTCTG ACTTGAGCGT CGATTTTTGT GATGCTCGTC AGGGGGCGG AGCCTATGGA
5641    AAAACGCCAG CAACGCGGCC TTTTTACGGT TCCTGGCCTT TTGCTGGCCT TTTGCTCACA
5701    TGTTCTTTCC TGCGTTATCC CCTGATTCTG TGGATAACCG TATTACCGCC TTTGAGTGAG
5761    CTGATACCGC TCGCCGCAGC CGAACGACCG AGCGCAGCGA GTCAGTGAGC GAGGAAGCGG
5821    AAGAGCGCCC AATACGCAAA CCGCCTCTCC CCGCGCGTTG GCCGATTCAT TAATGCAGCT
5881    GGCACGACAG GTTTCCCGAC TGGAAAGCGG GCAGTGAGCG CAACGCAATT AATGTGAGTT
5941    AGCTCACTCA TTAGGCACCC CAGGCTTTAC ACTTTATGCT TCCGGCTCGT ATGTTGTGTG
6001    GAATTGTGAG CGGATAACAA TTTCACACAG GAAACAGCTA TGACCATGAT TACGCCAAGC
6061    GCGCCGTTTA AACCCTCAGC TACCGATGTA CGGGCCAGAT ATCGCGTTG ACATTGATTA
6121    TTGACTAGTT ATTAATAGTA ATCAATTACG GGTCATTAG TTCATAGCCC ATATATGGAG
6181    TTCCGCGTTA CATAACTTAC GGTAAATGGC CCGCCTGGCT GACCGCCCAA CGACCCCGC
6241    CCATTGACGT CAATAATGAC GTATGTTCCC ATAGTAACGC CAATAGGGAC TTTCCATTGA
6301    CGTCAATGGG TGGACTATTT ACGGTAAACT GCCCACTTGG CAGTACATCA AGTGTATCAT
6361    ATGCCAAGTA CGCCCCCTAT TGACGTCAAT GACGGTAAAT GGCCCGCCTG GCATTATGCC
```

```
6421    CAGTACATGA CCTTATGGGA CTTTCCTACT TGGCAGTACA TCTACGTATT AGTCATCGCT
6481    ATTACCATGG TGATGCGGTT TTGGCAGTAC ATCAATGGGC GTGGATAGCG GTTTGACTCA
6541    CGGGGATTTC CAAGTCTCCA CCCCATTGAC GTCAATGGGA GTTTGTTTTG GCACCAAAAT
6601    CAACGGGACT TTCCAAAATG TCGTAACAAC TCCGCCCCAT TGACGCAAAT GGGCGGTAGG
6661    CGTGTACGGT GGGAGGTCTA TATAAGCAGA GCTCTCTGGC TAACTAGAGA ACCCACTGCT
6721    TACTGGCTTA TCGAAATTAA TACGACTCAC TATAGCAATT GCACGTGTGG CCACAGGTAA
6781    GTTTAAAGCT CAGGTCGAGA CCGGGCCTTT GTCCGGCGCT CCCTTGGAGC CTACCTAGAC
6841    TCAGCCGGCT CTCCACGCTT TGCCTGACCC TGCTTGCTCA ACTCTACGTC TTTGTTTCGT
                               AflII      HpaI       AvrII      EcoRV
                               ~~~~~~~    ~~~~~~     ~~~~~~     ~~~~~~
6901    TTTCTGTTCC TTTCTCTCCA CAGGCTTAAG AGTGTTAACG CGACCTAGGT AAGATATCCT
        KpnI
        ~~~~~~
        Acc65I    PacI       NotI       BstZ17I     SrfI        ApaI
        ~~~~~~    ~~~~~~~~   ~~~~~~~~   ~~~~~~      ~~~~~~~~    ~~~~~~
6961    TGGTACCGTG TTAATTAACT GGCGGCCGCT GTGTATACGT GGCCCGGGCT GGGGGCCCAT
        NheI      BglII      SphI
        ~~~~~~    ~~~~~~     ~~~~~~~
7021    AGCTAGCGTT AGATCTCTGG CATGC
```

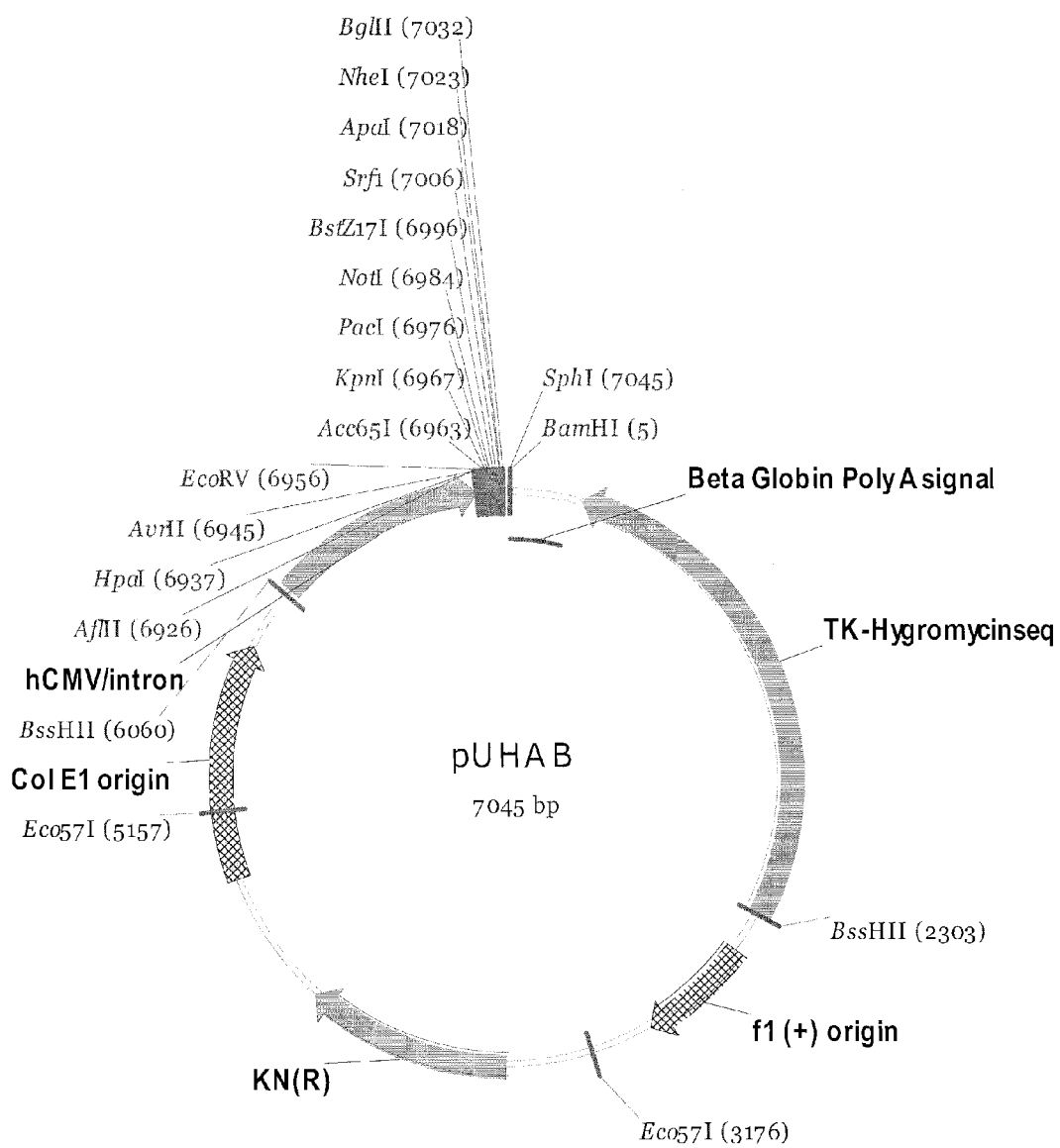
Figure 2: Plasmid Map of pUHAB

Figure 3: Vector A Sequence (a)

```
   1 TTAAGCCTGT GGAGAGAAAG GAACAGAAAA CGAAACAAAG ACGTAGAGTT GAGCAAGCAG
  61 GGTCAGGCAA AGCGTGGAGA GCCGGCTGAG TCTAGGTAGG CTCCAAGGGA GCGCCGGACA
 121 AAGGCCCGGT CTCGACCTGA GCTTTAAACT TACCTGTGGC CACACGTGCA ATTGCTATAG
 181 TGAGTCGTAT TAATTTCGAT AAGCCAGTAA GCAGTGGGTT CTCTAGTTAG CCAGAGAGCT
 241 CTGCTTATAT AGACCTCCCA CCGTACACGC CTACCGCCCA TTTGCGTCAA TGGGGCGGAG
 301 TTGTTACGAC ATTTTGGAAA GTCCCGTTGA TTTTGGTGCC AAAACAAACT CCCATTGACG
 361 TCAATGGGGT GGAGACTTGG AAATCCCCGT GAGTCAAACC GCTATCCACG CCCATTGATG
 421 TACTGCCAAA ACCGCATCAC CATGGTAATA GCGATGACTA ATACGTAGAT GTACTGCCAA
 481 GTAGGAAAGT CCCATAAGGT CATGTACTGG GCATAATGCC AGGCGGGCCA TTTACCGTCA
 541 TTGACGTCAA TAGGGGGCGT ACTTGGCATA TGATACACTT GATGTACTGC CAAGTGGGCA
 601 GTTTACCGTA AATACTCCAC CCATTGACGT CAATGGAAAG TCCCTATTGG CGTTACTATG
 661 GGAACATACG TCATTATTGA CGTCAATGGG CGGGGGTCGT TGGGCGGTCA GCCAGGCGGG
 721 CCATTTACCG TAAGTTATGT AACGCGGAAC TCCATATATG GGCTATGAAC TAATGACCCC
 781 GTAATTGATT ACTATTAATA ACTAGTCAAT AATCAATGTC AACGCGTATA TCTGGCCCGT
 841 ACATCGGTAG CTGAGGGTTT AAACGGCGCG CTTGGCGTAA TCATGGTCAT AGCTGTTTCC
 901 TGTGTGAAAT TGTTATCCGC TCACAATTCC ACACAACATA CGAGCCGGAA GCATAAAGTG
 961 TAAAGCCTGG GGTGCCTAAT GAGTGAGCTA ACTCACATTA ATTGCGTTGC GCTCACTGCC
1021 CGCTTTCCAG TCGGGAAACC TGTCGTGCCA GCTGCATTAA TGAATCGGCC AACGCGCGGG
1081 GAGAGGCGGT TTGCGTATTG GGCGCTCTTC CGCTTCCTCG CTCACTGACT CGCTGCGCTC
1141 GGTCGTTCGG CTGCGGCGAG CGGTATCAGC TCACTCAAAG GCGGTAATAC GGTTATCCAC
1201 AGAATCAGGG GATAACGCAG GAAAGAACAT GTGAGCAAAA GGCCAGCAAA AGGCCAGGAA
1261 CCGTAAAAAG GCCGCGTTGC TGGCGTTTTT CCATAGGCTC CGCCCCCCTG ACGAGCATCA
1321 CAAAAATCGA CGCTCAAGTC AGAGGTGGCG AAACCCGACA GGACTATAAA GATACCAGGC
1381 GTTTCCCCCT GGAAGCTCCC TCGTGCGCTC TCCTGTTCCG ACCCTGCCGC TTACCGGATA
1441 CCTGTCCGCC TTTCTCCCTT CGGGAAGCGT GGCGCTTTCT CATAGCTCAC GCTGTAGGTA
1501 TCTCAGTTCG GTGTAGGTCG TTCGCTCCAA GCTGGGCTGT GTGCACGAAC CCCCCGTTCA
1561 GCCCGACCGC TGCGCCTTAT CCGGTAACTA TCGTCTTGAG TCCAACCCGG TAAGACACGA
1621 CTTATCGCCA CTGGCAGCAG CCACTGGTAA CAGGATTAGC AGAGCGAGGT ATGTAGGCGG
1681 TGCTACAGAG TTCTTGAAGT GGTGGCCTAA CTACGGCTAC ACTAGAAGGA CAGTATTTGG
1741 TATCTGCGCT CTGCTGAAGC CAGTTACCTT CGGAAAAAGA GTTGGTAGCT CTTGATCCGG
1801 CAAACAAACC ACCGCTGGTA GCGGTGGTTT TTTTGTTTGC AAGCAGCAGA TTACGCGCAG
1861 AAAAAAAGGA TCTCAAGAAG ATCCTTTGAT CTTTTCTACG GGTCTGACG CTCAGTGGAA
1921 CGAAAACTCA CGTTAAGGGA TTTTGGTCAT GAGATTATCA AAAAGGATCT TCACCTAGAT
1981 CCTTTTAAAT TAAAAATGAA GTTTTAAATC AATCTAAAGT ATATATGAGT AAACTTGGTC
2041 TGACAGTTAC CAATGCTTAA TCAGTGAGGC ACCTATCTCA GCGATCTGTC TATTTCGTTC
2101 ATCCATAGTT GCCTGACTCC CCGTCGTGTA GATAACTACG ATACGGGAGG GCTTACCATC
2161 TGGCCCCAGT GCTGCAATGA TACCGCGAGA CCCACGCTCA CCGGCTCCAG ATTTATCAGC
2221 AATAAACCAG CCAGCCGGAA GGGCCGAGCG CAGAAGTGGT CCTGCAACTT TATCCGCCTC
2281 CATCCAGTCT ATTAATTGTT GCCGGGAAGC TAGAGTAAGT AGTTCGCCAG TTAATAGTTT
2341 GCGCAACGCC TGAATCGCCC CATCATCCAG CCAGAAAGTG AGGGAGCCAC GGTTGATGAG
2401 AGCTTTGTTG TAGGTGGACC AGTTGGTGAT TTTGAACTTT GCTTTGCCA CGGAACGGTC
2461 TGCGTTGTCG GAAGATGCG TGATCTGATC CTTCAACTCA GCAAAAGTTC GATTTATTCA
2521 ACAAAGCCGC CGTCCCGTCA AGTCAGCGTA ATGCTCTGCC AGTGTTACAA CCAATTAACC
2581 AATTCTGATT AGAAAAACTC ATCGAGCATC AAATGAAACT GCAATTTATT CATATCAGGA
2641 TTATCAATAC CATATTTTTG AAAAGCCGT TTCTGTAATG AAGGAGAAAA CTCACCGAGG
2701 CAGTTCCATA GGATGGCAAG ATCCTGGTAT CGGTCTGCGA TTCCGACTCG TCCAACATCA
2761 ATACAACCTA TTAATTTCCC CTCGTCAAAA ATAAGGTTAT CAAGTGAGAA ATCACCATGA
2821 GTGACGACTG AATCCGGTGA GAATGGCAAA AGCTTATGCA TTTCTTTCCA GACTTGTTCA
2881 ACAGGCCAGC CATTACGCTC GTCATCAAAA TCACTCGCAT CAACCAAACC GTTATTCATT
2941 CGTGATTGCG CCTGAGCGAG ACGAAATACG CGATCGCTGT TAAAAGGACA ATTACAAACA
3001 GGAATCGAAT GCAACCGGCG CAGGAACACT GCCAGCGCAT CAACAATATT TTCACCTGAA
3061 TCAGGATATT CTTCTAATAC CTGGAATGCT GTTTTCCCGG GGATCGCAGT GGTGAGTAAC
3121 CATGCATCAT CAGGAGTACG GATAAAATGC TTGATGGTCG GAAGAGGCAT AAATTCCGTC
3181 AGCCAGTTTA GTCTGACCAT CTCATCTGTA ACATCATTGG CAACGCTACC TTTGCCATGT
3241 TTCAGAAACA ACTCTGGCGC ATCGGGCTTC CCATACAATC GATAGATTGT CGCACCTGAT
3301 TGCCCGACAT TATCGCGAGC CCATTTATAC CCATATAAAT CAGCATCCAT GTTGGAATTT
3361 AATCGCGGCC TCGAGCAAGA CGTTTCCCGT TGAATATGGC TCATAACACC CCTTGTATTA

3421 CTGTTTATGT AAGCAGACAG TTTTATTGTT CATGATGATA TATTTTTATC TTGTGCAATG
3481 TAACATCAGA GATTTTGAGA CACAACGTGG CTTTGTTGAA TAAATCGAAC TTTTGCTGAG
3541 TTGAAGGATC AGATCACGCA TCTTCCCGAC AACGCAGACC GTTCCGTGGC AAAGCAAAAG
```

Figure 3 (cont)

(b)
```
3601 TTCAAAATCA CCAACTGGTC CACCTACAAC AAAGCTCTCA TCAACCGTGG CTCCCTCACT
3661 TTCTGGCTGG ATGATGGGGC GATTCAGGCG TTCTTCGGGG CGAAAACTCT CAAGGATCTT
3721 ACCGCTGTTG AGATCCAGTT CGATGTAACC CACTCGTGCA CCCAACTGAT CTTCAGCATC
3781 TTTTACTTTC ACCAGCGTTT CTGGGTGAGC AAAAACAGGA AGGCAAAATG CCGCAAAAAA
3841 GGGAATAAGG GCGACACGGA AATGTTGAAT ACTCATACTC TTCCTTTTTC AATATTATTG
3901 AAGCATTTAT CAGGGTTATT GTCTCATGAG CGGATACATA TTTGAATGTA TTTAGAAAAA
3961 TAAACAAATA GGGGTTCCGC GCACATTTCC CCGAAAAGTG CCACCTAAAT TGTAAGCGTT
4021 AATATTTTGT TAAAATTCGC GTTAAATTTT TGTTAAATCA GCTCATTTTT TAACCAATAG
4081 GCCGAAATCG GCAAAATCCC TTATAAATCA AAAGAATAGA CCGAGATAGG GTTGAGTGTT
4141 GTTCCAGTTT GGAACAAGAG TCCACTATTA AGAACGTGG ACTCCAACGT CAAAGGGCGA
4201 AAAACCGTCT ATCAGGGCGA TGGCCCACTA CGTGAACCAT CACCCTAATC AAGTTTTTTG
4261 GGGTCGAGGT GCCGTAAAGC ACTAAATCGG AACCCTAAAG GGAGCCCCCG ATTTAGAGCT
4321 TGACGGGGAA AGCCGGCGAA CGTGGCGAGA AAGGAAGGGA AGAAAGCGAA AGGAGCGGGC
4381 GCTAGGGCGC TGGCAAGTGT AGCGGTCACG CTGCGCGTAA CCACCACACC CGCCGCGCTT
4441 AATGCGCCGC TACAGGGCGC GTCCATTCG CCATTCAGGC TGCGCAACTG TTGGGAAGGG
4501 CGATCGGTGC GGGCCTCTTC GCTATTACGC CAGCTGGCGA AAGGGGGATG TGCTGCAAGG
4561 CGATTAAGTT GGGTAACGCC AGGGTTTTCC CAGTCACGAC GTTGTAAAAC GACGGCCAGT
4621 GAGCGCGCTG GCCGGCCTGT GCGAACGCCA GCAAGACGTA GCCCAGCGCG TCGGCCCCGA
4681 GATGCGCCGC GTGCGGCTGC TGGAGATGGC GGACGCGATG GATATGTTCT GCCAAGGGTT
4741 GGTTTGCGCA TTCACAGTTC TCCGCAAGAA TTGATTGGCT CCAATTCTTG GAGTGGTGAA
4801 TCCGTTAGCG AGGTGCCGCC CTGCTTCATC CCCGTGGCCC GTTGCTCGCG TTTGCTGGCG
4861 GTGTCCCCGG AAGAAATATA TTTGCATGTC TTTAGTTCTA TGATGACACA AACCCCGCCC
4921 AGCGTCTTGT CATTGGCGAA TTCGAACACG CAGATGCAGT CGGGGCGGCG CGGTCCGAGG
4981 TCCACTTCGC ATATTAAGGT GACGCGTGTG GCCTCGAACA CCGAGCGACC CTGCAGCGAC
5041 CCGCTTAACA GCGTCAACAG CGTGCCGCAG ATCCCGGGGG GCAATGAGAT ATGAAAAGC
5101 CTGAACTCAC CGCGACGTCT GTCGAGAAGT TTCTGATCGA AAAGTTCGAC AGCGTCTCCG
5161 ACCTGATGCA GCTCTCGGAG GGCGAAGAAT CTCGTGCTTT CAGCTTCGAT GTAGGAGGGC
5221 GTGGATATGT CCTGCGGGTA AATAGCTGCG CCGATGGTTT CTACAAAGAT CGTTATGTTT
5281 ATCGGCACTT TGCATCGGCC GCGCTCCCGA TTCCGGAAGT GCTTGACATT GGGGAATTCA
5341 GCGAGAGCCT GACCTATTGC ATCTCCCGCC GTGCACAGGG TGTCACGTTG CAAGACCTGC
5401 CTGAAACCGA ACTGCCCGCT GTTCTGCAGC CGGTCGCGGA GGCCATGGAT GCGATCGCTG
5461 CGGCCGATCT TAGCCAGACG AGCGGGTTCG GCCCATTCGG ACCGCAAGGA ATCGGTCAAT
5521 ACACTACATG GCGTGATTTC ATATGCGCGA TTGCTGATCC CCATGTGTAT CACTGGCAAA
5581 CTGTGATGGA CGACACCGTC AGTGCGTCCG TCGCGCAGGC TCTCGATGAG CTGATGCTTT
5641 GGGCCGAGGA CTGCCCCGAA GTCCGGCACC TCGTGCACGC GGATTTCGGC TCCAACAATG
5701 TCCTGACGGA CAATGGCCGC ATAACAGCGG TCATTGACTG GAGCGAGGCG ATGTTCGGGG
5761 ATTCCCAATA CGAGGTCGCC AACATCTTCT TCTGGAGGCC GTGGTTGGCT TGTATGGAGC
5821 AGCAGACGCG CTACTTCGAG CGGAGGCATC CGGAGCTTGC AGGATCGCCG CGGCTCCGGG
5881 CGTATATGCT CCGCATTGGT CTTGACCAAC TCTATCAGAG CTTGGTTGAC GGCAATTTCG
5941 ATGATGCAGC TTGGGCGCAG GGTCGATGCG ACGCAATCGT CCGATCCGGA GCCGGGACTG
6001 TCGGGCGTAC ACAAATCGCC CGCAGAAGCG CGGCCGTCTG GACCGATGGC TGTGTAGAAG
6061 TACTCGCCGA TAGTGGAAAC CGACGCCCCA GCACTCGTCC GGATCGGGAG ATGGGGGAGG
6121 CTAACTGAAA CACGGAAGGA GACAATACCG GAAGGAACCC GCGCTATGAC GGCAATAAAA
6181 AGACAGAATA AAACGCACGG GTGTTGGGTC GTTTGTTCAT AAACGCGGGG TTCGGTCCCA
6241 GGGCTGGCAC TCTGTCGATA CCCCACCGAG ACCCCATTGG GGCCAATACG CCCGCGTTTC
6301 TTCCTTTTCC CCACCCCACC CCCCAAGTTC GGGTGAAGGC CCAGGGCTCG CAGCCAACGT
6361 CGGGGCGGCA GGCCCTGCCA TAGCCACTGG CCCCGTGGGT TAGGGACGGG GTCCCCCATG
6421 GGGAATGGTT TATGGTTCGT GGGGGTTATT ATTTTGGGCG TTGCGTGGGG TCAGGTCCAC
6481 GACTGGACTG AGCAGACAGA CCCATGGTTT TTGGATGGCC TGGGCATGGA CCGCATGTAC
6541 TGGCGCGACA CGAACACCGG GCGTCTGTGG CTGCCAAACA CCCCCGACCC CCAAAAACCA
6601 CCGCGCGGAT TTCTGGCGTG CCAAGCTAGT CGAAAGCTTG GCCGGCCTGT ACATGATCAA
6661 CGCGTGAGCT CTCTAGAGCT TGTCGACAGA TCCCCCTCTT CATTTCTTTA TGTTTTAAAT
6721 GCACTGACCT CCCACATTCC CTTTTTAGTA AAATATTCAG AAATAATTTA AATACATCAT
6781 TGCAATGAAA ATAAATGTTT TTTATTAGGC AGAATCCAGA TGCTCAAGGC CCTTCATAAT
6841 ATCCCCCAGT TTAGTAGTTA GACTTAGGGA ACAAAGGAAC CTTTAATAGA AATTGGACAG
6901 CAAGAAAGCG AGGGGGATCT GGATCCTCCG GACCCGTATC TAGAATCATC GATTCATTTA
6961 CCCGGAGACA GGGAGAGGCT CTTCTGCGTG TAGTGGTTGT GCAGAGCCTC ATGCATCACG
7021 GAGCATGAGA AGACGTTCCC CTGCTGCCAC CTGCTCTTGT CCACGGTGAG CTTGCTGTAG
7081 AGGAAGAAGG AGCCGTCGGA GTCCAGCACG GGAGGCGTGG TCTTGTAGTT GTTCTCCGGC
7141 TGCCCATTGC TCTCCCACTC CACGGCGATG TCGCTGGGAT AGAAGCCTTT GACCAGGCAG
7201 GTCAGGCTGA CCTGGTTCTT GGTCAGCTCA TCCCGGGATG GGGCAGGGT GTACACCTGT
7261 GGTTCTCGGG GCTGCCCTTT GGCTTTGGAG ATGGTTTTCT CGATGGGGGC TGGGAGGGCT
```

Figure 3 (cont)

(c)
```
7321 TTGTTGGAGA CCTTGCACTT GTACTCCTTG CCATTCAGCC AGTCCTGGTG CAGGACGGTG
7381 AGGACGCTGA CCACACGGTA CGTGCTGTTG TACTGCTCCT CCCGCGGCTT TGTCTTGGCA
7441 TTATGCACCT CCACGCCGTC CACGTACCAG TTGAACTTGA CCTCAGGGTC TTCGTGGCTC
7501 ACGTCCACCA CCACGCATGT GACCTCAGGG GTCCGGGAGA TCATGAGGGT GTCCTTGGGT
7561 TTTGGGGGGA AGAGGAAGAC TGACGGTCCC CCCAGGAGTT CAGGTGCTGG GCACGGTGGG
7621 CATGTGTGAG TTTTGTCACA AGATTTGGGC TCAACTTTCT TGTCCACCTT GGTGTTGCTG
7681 GGCTTGTGAT TCACGTTGCA GATGTAGGTC TGGGTGCCCA AGCTGCTGGA GGGCACGGTC
7741 ACCACGCTGC TGAGGGAGTA GAGTCCTGAG GACTGTAGGA CAGCCGGGAA GGTGTGCACG
7801 CCGCTGGTCA GGGCGCCTGA GTTCCACGAC ACCGTCACCG GTTCGGGGAA GTAGTCCTTG
7861 ACCAGGCAGC CCAGGGCCGC TGTGCCCCCA GAGGTGCTCT TGGAGGAGGG TGCCAGGGGG
7921 AAGACCGATG GGCCCTTGGT GCTAGCGGAG CTCACGGTCA CCAGGGTGCC CTGTCCCCAG
7981 GCATCCATGA AGTAGTTCTC GTAATAGTAG TCGGTGATGT ATGCATTTCT GGCACAGTAA
8041 TACACAGCGG TGTCGGCAGC GGTCACGCTG CTCAGCTTCA GGCTGAACTG GTTCTTGGAG
8101 GTGTCCACGG AGATGGTCAC GCGGCTCTTG AAGGCGCTGT TATAGTCAGT GCCGCCTTGA
8161 TTCCAAATGA TGCCGATCCA CTCCAGTCCC TTGCCTGGAG GCTGTCTGAT CCAGCTCACG
8221 CTGTGGCTGG GCAGGCTGAA TCCAGACACG GTACAGGTCA GGCTCAGGGT CTCGCTAGGC
8281 TTCACCAGGC CTGGTCCAGA CTCCTGCAGC TGCACCTGGG ACAGCACACA GCTTGGGAAT
8341 GTCACCAGGC AGAACAGCAG CCCCAGCACA GCCATGGTGG CGGCAGTACT C
```

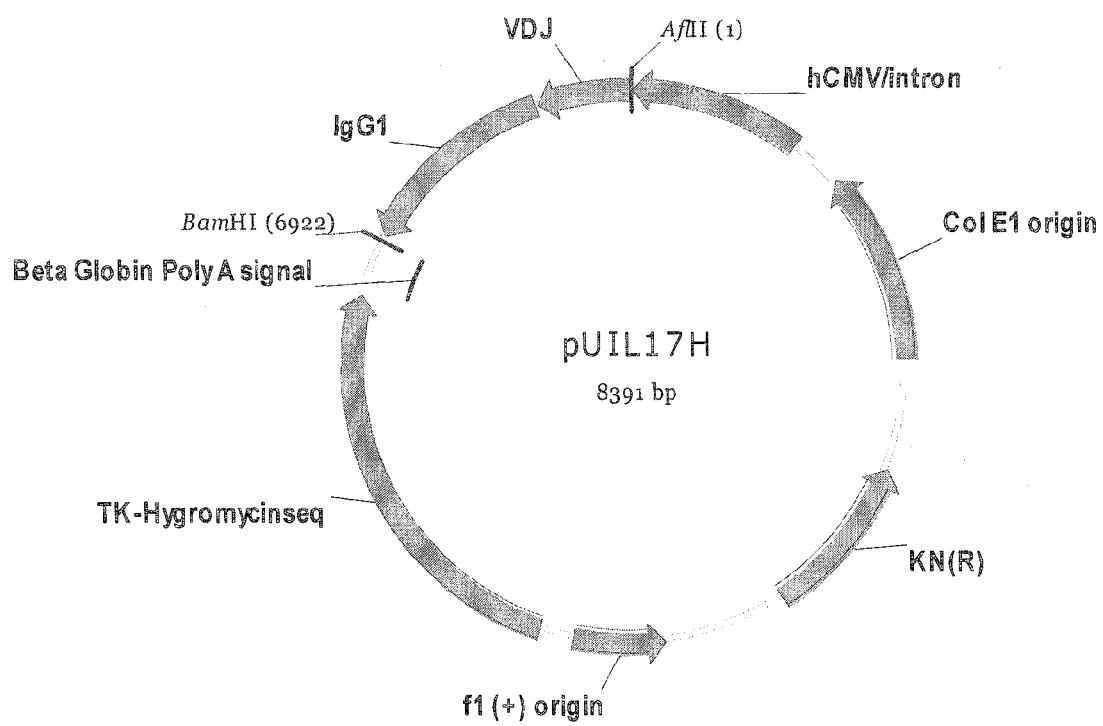
Figure 4: Plasmid Map of Vector A

MAMMALIAN EXPRESSION VECTOR PUHAB

This application claims the benefit of U.S. provisional patent application no. 61/113,824; filed Nov. 12, 2008; which is herein incorporated by reference in its entirety.

FIELD OF THE INVENTION

The present invention relates to the construction and utilization of a new mammalian expression vector that contains a unique multiple cloning site (MCS), designated pUHAB. The pUHAB vector comprises a high copy replication origin (ColE1), a drug resistance gene (TK-Hygromycin), and a human cytomegalovirus promoter operably associated with a unique intron (hCMV/intron). Further, pUHAB comprises a selectable marker conferring resistance to kanamycin in bacterial cells, and a phage f1(+) region. pUHAB can be used to transiently or stably express cloned genes when transfected into mammalian cells. The invention also encompasses kits and host cells and cell lines comprising pUHAB, and methods of producing a recombinant protein using pUHAB.

BACKGROUND OF THE INVENTION

Culturing cells for the commercial production of therapeutic proteins is a costly process. The equipment required is expensive and research and development and production costs are high. Development of cell culture processes which maximize the quantity of therapeutic protein produced per liter of cell culture will minimize the resources necessary to produce a given quantity of the protein. It is, thus, desirable to use commercially viable reagents which produce large quantities of proteins.

Many naturally occurring cells do not produce large quantities of desired proteins, under standard culture conditions. Rather, extensive research and development of cell culture processes, which coax cells in culture to generate large quantities of therapeutic protein, must be performed. Typically, identifying plasmid vectors useful for expressing a protein at a high level requires a significant amount of inventive input.

SUMMARY OF THE INVENTION

The present invention provides, in part, a new expression vector. In one embodiment, the invention provides a vector characterized by a long and unique multiple cloning site. The multiple cloning site may comprise 10, 11, 12, 13, 14 or 15 restriction sites selected from the group consisting of: AflII, HpaI, AvrII, EcoRV, Acc651, KpnI, PacI, NotI, BstZ17I, SrfI, ApaI, NheI, BglII, SphI and BamHI. In one embodiment, the multiple cloning site comprises all of said restriction sites, e.g., in the order: 5'-AflII-HpaI-AvrII-EcoRV-Acc651-Kpn1-PacI-NotI-BstZ17I-SrfI-ApaI-NheI-BglII-SphI-BamHI-3'. In an exemplary embodiment, the multiple cloning site comprises the nucleotide sequence set forth in SEQ ID NO: 2.

The vector may further comprise a promoter located upstream of or within the multiple cloning site. In one embodiment, the promoter is the human cytomegalovirus (hCMV) promoter. The promoter may be operably associated with an intron that enhances expression from the promoter. In one embodiment, the nucleotide sequence of the intron is comprised by the nucleotide sequence of SEQ ID NO: 1.

The vector may further comprise at least 1, 2, 3 or 4 elements selected from the group consisting of: a selectable marker for eukaryotic cells (e.g., a TK-Hygromycin gene); a prokaryotic origin of replication (e.g., a ColE1 origin of replication); a bacterial drug resistance marker (e.g., a kanamycin resistance gene); and a phage f1 region (e.g., a phage f1(+) region). In one embodiment, the vector comprises all of these elements. The vector may further comprise a terminator/polyA addition site.

The invention also provides a vector comprising an hCMV promoter operably associated with an intron that enhances expression from said promoter, wherein the nucleotide sequence of the intron is comprised by the nucleotide sequence of SEQ ID NO: 1. The vector may further comprise at least 1, 2, 3, 4 or 5 elements selected from the group consisting of: a multiple cloning site (e.g., the multiple cloning site of SEQ ID NO: 2); a selectable marker for eukaryotic cells (e.g., a TK-Hygromycin gene); a prokaryotic origin of replication (e.g., a ColE1 origin of replication); a bacterial drug resistance marker (e.g., a kanamycin resistance gene); and a phage f1 region (e.g., a phage f1(+) region). In one embodiment, the vector comprises all of these elements. The vector may further comprise a terminator/polyA addition site.

In an exemplary embodiment, the vector comprises the nucleotide sequence set forth in SEQ ID NO: 1.

The vector of the invention may be an expression vector for use in expression of a recombinant polypeptide in a mammalian host cell or organism. In this embodiment, the vector comprises a heterologous DNA sequence encoding the recombinant polypeptide, wherein the heterologous DNA sequence is operably linked to the promoter sequence.

The invention also provides a host cell comprising the vector of the invention. Also encompassed is a method for producing a recombinant polypeptide in a mammalian host cell, comprising introducing the vector of the invention into the host cell under conditions which allow for expression of the polypeptide. The recombinant polypeptide may then be purified.

The invention also provides a kit comprising the vector of the invention.

BRIEF DESCRIPTION OF THE FIGURES

FIG. 1 (a-c). Nucleotide sequence of pUHAB (SEQ ID NO: 1).

FIG. 2. Plasmid map of pUHAB.

| Feature Map | | |
| --- | --- | --- |
| Element | Start | End |
| Beta Globin polyA signal | 5 | 243 |
| TK-Hygromycin | 289 | 2298 |
| f1(+) origin | 2467 | 2923 |
| KN(R) (Tn903 type I) | 3523 | 4339 |
| ColE1 origin | 4884 | 5824 |
| hCMV/intron | 6084 | 6925 |
| MCS | 6926 | 5 |

FIG. 3 (a-c). Nucleotide sequence of Vector A (SEQ ID NO: 3).

FIG. 4. Plasmid map of Vector A.

| Feature Map | | |
| --- | --- | --- |
| Element | Start | End |
| hCMV/intron (complementary) | 5 | 846 |

-continued

Feature Map

| Element | Start | End |
|---|---|---|
| ColE1 origin (complementary) | 1106 | 2046 |
| KN(R) (Tn903 type I) (complementary) | 2591 | 3407 |
| f1(+) origin (complementary) | 4007 | 4463 |
| TK-Hygromycin | 4632 | 6641 |
| Beta Globin polyA signal (complementary) | 6687 | 6925 |
| IgG1 constant (complementary) | 6950 | 7930 |
| VDJ (variable region) (complementary) | 7942 | 8391 |

DETAILED DESCRIPTION OF THE INVENTION

The present invention provides an expression vector useful for recombinant protein expression in any cell, for example in a mammalian cell, a bacterial cell, a yeast cell or an insect cell. The vector may be used to transiently or stably express a broad range of recombinant proteins. The multiple cloning site of the vector offers many common and rare restriction sites to accommodate a variety of expression cassettes.

The present invention includes a vector comprising or consisting of the nucleotide sequence of SEQ ID NO: 1.

Molecular Biology

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide," "nucleic acid" or "nucleic acid molecule" includes the polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"). Polynucleotides of the invention can be in any form, including circular, linear, double-stranded or single-stranded.

A "polynucleotide sequence," "nucleic acid sequence" or "nucleotide sequence" is a series of nucleotides in a nucleic acid, such as DNA or RNA, and means any chain of two or more nucleotides.

A "coding sequence" or a sequence "encoding" an expression product, such as a RNA or peptide, is a nucleotide sequence that, when expressed, results in production of the product.

The term "gene" means a DNA sequence that codes for or corresponds to a particular sequence of ribonucleotides or amino acids which comprise all or part of one or more RNA molecules or proteins, and may or may not be operably linked to regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 300 nucleotides (e.g., 30, 40, 50, 60, 70, 80, 90, 150, 175, 200, 250 or 300), that may be hybridizable to a genomic DNA molecule, a cDNA molecule, or an mRNA molecule encoding a gene, mRNA, cDNA, or other nucleic acid of interest. Oligonucleotides are usually single-stranded, but may be double-stranded. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, e.g., on a nucleic acid synthesizer.

A "protein sequence," "peptide sequence" or "polypeptide sequence," or "amino acid sequence" refers to a series of two or more amino acids in a protein, peptide or polypeptide.

"Protein," "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

As used herein, the term "functional variant" refers to a variant nucleotide or polypeptide that produces substantially the same biological effect as the original nucleotide or polypeptide.

Variants included in the invention may contain individual substitutions, deletions or additions to the original nucleic acid or polypeptide sequences. Such changes will alter, add or delete a single amino acid or a small percentage of amino acids (e.g., 1%, 2%, 3%, 4%, 5%, 6%, 7%, 8%, 9% or 10%) in the encoded sequence. Variants are referred to as "conservatively modified variants" where the alteration results in the substitution of an amino acid with a chemically similar amino acid.

"PCR amplification" of DNA as used herein includes the use of polymerase chain reaction (PCR) to increase the concentration of a particular DNA sequence within a mixture of DNA sequences. For a description of PCR see Saiki et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA or a protein. For example, a host cell may be a mammalian cell, a bacterial cell, a yeast cell or an insect cell.

A further aspect of the present invention relates to a host cell or host cell line comprising the vector of the invention. In one embodiment, the host cell is a mammalian cell. Examples of mammalian host cells include, by way of nonlimiting example, Chinese hamster ovary (CHO) cells, CHO-K1 cells, CHO-DXB-11 cells, CHO-DG44 cells, bovine mammary epithelial cells, mouse Sertoli cells, canine kidney cells, buffalo rat liver cells, human lung cells, mouse mammary tumor cells, rat fibroblasts, bovine kidney (MDBK) cells, NSO cells, SP2 cells, TRI cells, MRC 5 cells, FS4 cells, HEK-293T cells, NIH-3T3 cells, HeLa cells, baby hamster kidney (BHK) cells, African green monkey kidney (COS) cells, human hepatocellular carcinoma (e.g., Hep G2) cells, A549 cells, etc. In one embodiment, the mammalian host cell is a human host cell. Mammalian host cells can be cultured according to methods known in the art (see, e.g., J. Immunol. Methods 56:221 (1983), *Animal Cell Culture: A Practical Approach* 2nd Ed Rickwood, D. and Hames, B. D., eds. Oxford University Press, New York (1992)).

Vectors of the invention can also be introduced into a bacterial cell. In one embodiment, competent *E. coli* are transformed. Examples of suitable *E. coli* include DH1, DH5, DH5α, XL1-Blue, SURE, SCS110, OneShot Top 10, and HB101.

Vectors of the invention may be introduced into host cells according to any of the many techniques known in the art, e.g., dextran-mediated transfection, polybrene-mediated transfection, protoplast fusion, electroporation, calcium phosphate co-precipitation, lipofection, direct microinjection of the vector into nuclei, or any other means appropriate for a given host cell type.

A "cassette" or an "expression cassette" refers to a DNA coding sequence or segment of DNA that codes for an expression product (e.g., peptide or RNA) that can be inserted into a vector, e.g., at defined restriction sites. The expression cassette may comprise a promoter and/or a terminator and/or polyA signal operably linked to the DNA coding sequence.

The sequence of a nucleic acid may be determined by any method known in the art (e.g., chemical sequencing or enzymatic sequencing). "Chemical sequencing" of DNA includes methods such as that of Maxam and Gilbert (Proc. Natl. Acad. Sci. USA (1977) 74:560), in which DNA is randomly cleaved using individual base-specific reactions. "Enzymatic sequencing" of DNA includes methods such as that of Sanger (Sanger et al., Proc. Natl. Acad. Sci. USA (1977) 74:5463).

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with or operably linked to other expression control sequences, including enhancer and repressor sequences or with a nucleic acid to be expressed. An expression control sequence is operably associated with or operably linked to a promoter if it regulates expression from said promoter.

Promoters which may be used to control gene expression include, but are not limited to, SRα promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), the mouse CMV immediate early promoter, the SV40 early promoter region (Benoist at al., Nature 290:304-310 (1981)), the *Orgyia pseudotsugata* immediate early promoter, the herpes thymidine kinase promoter (Wagner at al., Proc. Natl. Acad. Sci. USA 78:1441-1445 (1981)), the regulatory sequences of the metallothionein gene (Brinster et al., Nature 296:39-42 (1982)); prokaryotic expression vectors such as the β-lactamase promoter (Villa-Komaroff et al., Proc. Natl. Acad. Sci. USA 75:3727-3731 (1978)), or the tac promoter (DeBoer et al., Proc. Natl. Acad. Sci. USA 80:21-25 (1983)); and promoter elements from yeast or other fungi such as the GAL1, GAL4 or GAL10 promoter, the ADH (alcohol dehydrogenase) promoter, PGK (phosphoglycerol kinase) promoter or the alkaline phosphatase promoter.

Viral long terminal repeat promoters such as the mouse mammary tumor virus long terminal repeat (MMTV-LTR) (Fasel et al, EMBO J. 1(1):3-7 (1982)), the moloney murine sarcoma virus long terminal repeat (Reddy et al., Proc. Natl. Acad. Sci. USA 77(9): 5234-5238 (1980)), the moloney murine leukemia virus long terminal repeat (Van Beveren at al., Proc. Natl. Acad. Sci. USA 77(6): 3307-3311 (1980)), the HIV LTR (Genbank Accession No. AB100245), the bovine foamy virus LTR (Genbank Accession No. NC_001831), RSV 5'-LTR (Genbank Accession No. K00087), the HIV-2 LTR (Genbank Accession No. NC_001722), an avian retroviral LTR (Ju at al., Cell 22: 379-386 (1980)) and the human herpesvirus LTR (Genbank Accession No. NC_001806) may be included in the vectors of the present invention.

Other acceptable promoters include the human CMV promoter, the human CMV5 promoter, the murine CMV promoter, the EF1α promoter, the SV40 promoter, a hybrid CMV promoter for liver specific expression (e.g., made by conjugating CMV immediate early promoter with the transcriptional promoter elements of either human α1-antitrypsin (HAT) or albumin (HAL) promoter), or promoters for hepatoma specific expression (e.g., wherein the transcriptional promoter elements of either human albumin (HAL; about 1000 bp) or human α1-antitrypsin (HAT, about 2000 bp) are combined with a 145 bp long enhancer element of human α1-microglobulin and bikunin precursor gene (AMBP); HAL-AMBP and HAT-AMBP).

In addition, bacterial promoters, such as the T7 RNA Polymerase promoter or the tac promoter, may be used to control expression.

In one embodiment, the promoter is the human CMV (hCMV) promoter. The hCMV promoter provides a high level of expression in a variety of mammalian cell types.

A coding sequence is "under the control of", "functionally associated with", "operably linked to" or "operably associated with" transcriptional and translational control sequences in a cell when the sequences direct or regulate expression of the sequence. For example, a promoter operably linked to a gene will direct RNA polymerase mediated transcription of the coding sequence into RNA, preferably mRNA, which may then be spliced (if it contains introns) and, optionally, translated into a protein encoded by the coding sequence. A terminator/polyA signal operably linked to a gene terminates transcription of the gene into RNA and directs addition of a polyA signal onto the RNA.

The terms "express" and "expression" mean allowing or causing the information in a gene, RNA or DNA sequence to become manifest; for example, producing a protein by activating the cellular functions involved in transcription and translation of a corresponding gene. "Express" and "expression" include transcription of DNA to RNA and of RNA to protein. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. Examples of transformation methods which are very well known in the art include liposome delivery, electroporation, CaPO<sub>4</sub> transformation, DEAE-Dextran transformation, microinjection and viral infection.

The present invention includes vectors which comprise polynucleotides of the invention. The term "vector" may refer to a vehicle (e.g., a plasmid) by which a DNA or RNA sequence can be introduced into a host cell, so as to transform the host and, optionally, promote expression and/or replication of the introduced sequence.

The polynucleotides of the invention may be expressed in an expression system. The term "expression system" means a host cell and compatible vector which, under suitable conditions, can express a protein or nucleic acid which is carried by the vector and introduced to the host cell. Common expression systems include *E. coli* host cells and plasmid vectors, insect host cells and baculovirus vectors, and mammalian host cells and vectors such as plasmids, cosmids, BACs, YACs and viruses such as adenovirus and adenovirus associated virus (AAV).

Vectors

The invention provides a new expression vector. In one embodiment, the vector comprises a unique and long multiple cloning site that provides the vector with the flexibility to incorporate a variety of recombinant genes in complex arrangements for expression in a mammalian cell or organism. In one embodiment, the vector comprises a multiple cloning site comprising restriction sites selected from the group consisting of: AflII, HpaI, AvrII, EcoRV, Acc651, KpnI, PacI, NotI, BstZ17I, SrfI, ApaI, NheI, BglII, SphI, and BamHI. The multiple cloning site may comprise 10, 11, 12, 13, 14 or 15 of said restriction sites. The multiple cloning site may comprise, for example, the nucleotide sequence of SEQ ID NO: 2 as shown below:

```
                                            (SEQ ID NO: 2)
                                           KpnI
   AflII     HpaI      AvrII    EcoRV      Acc651
   -------   -----     ------   ------     ------
   CTTAAGAGTG TTAACGCGAC CTAGGTAAGA TATCCTTGGT ACCGTG

-continued
   PacI       NotI      BstZ17I    SrfI      ApaI
   -------   ---------  -------   ---------  -----
   TTAATTAACTGGCG GCCGCTGTGT ATACGTGGCC CGGGCTGGGG GC NheI       BglII     SphI       BamHI
   --------   -------   -------     ------
   CCATAGCT AGCGTTAGATC TCTGGCATG CGCTGGATCC
```

The present invention contemplates vectors comprising the above-indicated multiple cloning site in the orientation shown or in the opposite orientation.

In one embodiment of the invention, the vector comprises a promoter which is essentially any RNA polymerase-dependent promoter, e.g., an RNA polymerase II-dependent promoter.

In certain embodiments, the vector may comprise a combination of a promoter and an intron that increases gene expression from said promoter. The intron may be synthetic or naturally-derived. In one embodiment, the intron increases gene expression from the hCMV promoter. In an exemplary embodiment, the intron is a unique intron including the nucleotide sequence:

```
                                            (SEQ ID NO: 4)
   CA GGTAAGTTTA AAGCTCAGGT CGAGACCGGG CCTTTGTCCG

GCGCTCCCTT GGAGCCTACC TAGACTCAGC CGGCTCTCCA

CGCTTTGCCT GACCCTGCTT GCTCAACTCT ACGTCTTTGT

TTCGTTTTCT GTTCCTTTCT CTCCACAGGC.
```

The combination of the human CMV promoter and the intron (hCMV/intron) provides higher expression levels than those achieved by using hCMV alone.

The vector may also include one or more further regulatory elements in addition to the promoter and the intron, such as enhancer elements, splicing signals, polyadenylation signals, termination signals, RNA export elements, secretion signals, internal ribosome entry sites, and the like.

In one embodiment, the vector of the invention comprises a selective marker which allows for selection of eukaryotic (e.g., mammalian) host cells into which the vector has been introduced. The selective marker may, for example, confer resistance to drugs such as G418, hygromycin or methotrexate. In one embodiment of the invention, the selective marker is a gene providing positive selection for hygromycin resistance in both prokaryotes and eukaryotes, fused to the thymidine kinase promoter (TK-Hygromycin).

In one embodiment, the vector of the invention comprises a prokaryotic antibiotic resistance marker such as the ampicillin resistance gene or the kanamycin resistance gene.

In one embodiment, the vector of the invention comprises a phage f1 region comprising the origin of replication from the f1 filamentous phage, allowing rescue of single-stranded DNA upon co-infection with helper phage. This single-stranded DNA may be used for, e.g., dideoxynucleotide sequencing or site-directed mutagenesis. In one embodiment, the phage f1 region is a phage f1(+) region.

In certain embodiments of the invention, the vector is a plasmid. The plasmid vector may comprise a prokaryotic origin of replication to allow autonomous replication within a prokaryotic host cell. In one embodiment, the prokaryotic origin of replication is the high copy ColE1 origin of replication, which allows the vector to produce the high levels of plasmid DNA required for large scale transient transfections.

In an embodiment of the invention, the vector comprises a multiple cloning site of SEQ ID NO: 2, a ColE1 high copy origin of replication, a TK-Hygromycin drug resistance gene, a human CMV promoter operably associated with an intron, a kanamycin resistance marker, and a phage f1(+) region. The invention also encompasses vectors wherein any or all of these elements are replaced by functional variants of said elements. In one embodiment, the vector is described by the plasmid map of FIG. 2.

In one embodiment of the invention, the vector is an expression vector capable of expressing a recombinant polypeptide in a host cell or organism. In an exemplary embodiment, the host cell or organism is a mammalian host cell or organism.

The expression vector comprises, in an embodiment of the invention, a terminator sequence to terminate transcription. Further, the expression vector may comprise a polyadenylation (polyA) signal for stabilization and processing of the 3' end of an mRNA transcribed from the promoter. PolyA signals include, for example, the rabbit beta globin polyA signal or the bovine growth hormone polyA signal, as well as polyA signals of viral origin, such as the SV40 late polyA region. In one embodiment of the invention, the vector comprises a chicken beta globin terminator/polyA signal. The multiple cloning site of the vector may be located between the promoter and the polyA signal. In some embodiments, restriction sites may also be included downstream of the polyA signal.

The vector may contain more than one expression cassette to allow for expression of multiple recombinant polypeptides from a single vector. In certain embodiments, the vector comprises 1, 2, 3, 4 or 5 expression cassettes.

In an exemplary embodiment, the vector is pUHAB. The expression "pUHAB" refers to a vector comprising of the nucleotide sequence of SEQ ID NO: 1 (as shown in FIG. 1). The multiple cloning site of the pUHAB vector is flexible enough to incorporate a variety of recombinant genes in complex, multicistronic arrangements for expression in mammalian cells. Further, two expression cassettes containing the gene of interest and the TK-Hygromycin drug resistance gene can be transferred together from the vector of the invention to a different vector using either Eco571 or BssHII restriction enzymes to generate a new vector containing more than two mammalian expression cassettes.

Transfection may result in transiently transfected cell lines, in which the vector is maintained episomally and has not integrated into the genome. Transfection may also result in stably transfected cell lines, in which parts of the vector are stably integrated into the genome of the host cell, e.g., by random, non-homologous recombination events. A stable transfection may result in loss of parts of the vector sequence that are not directly related to expression of the recombinant gene product, e.g., bacterial copy number control regions. Accordingly, a stably transfected host cell is defined as a host cell that has integrated at least part or different parts of the expression vector into its genome.

Genes

Any of several genes may be inserted into the plasmids of the present invention, for example, immunoglobulins, e.g., which bind specifically to IGF1R. Plasmids of the present invention encoding any of the following target immunoglobulin amino acid sequences form part of the present invention.

19D12/15H12 Light Chain (SEQ ID NO: 5)

MSPSQLIGFLLLWVPASRGEIVLTQVPDFQSVTPKEKVTITCRASQSIG
SSLHWYQQKPDQSPKLLIKYASQSLSGVPSRFSGSGSGTDFTLTINSLE
AEDAAAYYCHQSSRLPHTFGGGTKVEIKRT

19D12/15H12 Heavy Chain (SEQ ID NO: 6)

MEFGLSWVFLVAILKGVQCEVQLVQSGGGLVHPGGSLRLSCAASGFTFS
SFAMHWVRQAPGKGLEWISVIDTRGATYYADSVKGRFTISRDNAKNSLY
LQMNSLRAEDMAVYYCARLGNFYYGMDVWGQGTTVTVSS

19D12/15H12 Light Chain-C (LCC) (SEQ ID NO: 7)

M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D A
A A Y Y C H Q S S R L P H T F G Q
G T K V E I K R T

19D12/15H12 Light Chain-D (LCD) (SEQ ID NO: 8)

M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D F
A V Y Y C H Q S S R L P H T F G Q
G T K V E I K R T

19D12/15H12 Light Chain-E (LCE) (SEQ ID NO: 9)

M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D A
A V Y Y C H Q S S R L P H T F G Q
G T K V E I K R T

19D12/15H12 Light Chain-F (LCF) (SEQ ID NO: 10)

M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D F
A V Y Y C H Q S S R L P H T F G Q
G T K V E I K R T

-continued

19D12/15H12 heavy chain-A (HCA) (SEQ ID NO: 11)

<u>Met Glu Phe Gly Leu Ser Trp Val Phe Leu Val Ala Ile</u>
<u>Leu Lys Gly Val Gln Cys</u> Glu Val Gln Leu Val Gln Ser
Gly Gly Gly Leu Val Lys Pro Gly Ser Leu Arg Leu
Ser Cys Ala Ala Ser Gly Phe Thr Phe <u>Ser Ser Phe Ala</u>
<u>Met His</u> Trp Val Arg Gln Ala Pro Gly Lys Gly Leu Glu
Trp Ile Ser <u>Val Ile Asp Thr Arg Gly Ala Thr Tyr Tyr</u>
<u>Ala Asp Ser Val Lys Gly</u> Arg Phe Thr Ile Ser Arg Asp
Asn Ala Lys Asn Ser Leu Tyr Leu Gln Met Asn Ser Leu
Arg Ala Glu Asp Thr Ala Val Tyr Tyr Cys Ala Arg <u>Leu</u>
<u>Gly Asn Phe Tyr Tyr Gly Met Asp Val</u> Trp Gly Gln Gly
Thr Thr Val Thr Val Ser Ser

19D12/15H12 heavy chain-B (HCB) (SEQ ID NO: 12)

<u>Met Glu Phe Gly Leu Ser Trp Val Phe Leu Val Ala Ile</u>
<u>Leu Lys Gly Val Gln Cys</u> Glu Val Gln Leu Val Gln Ser
Gly Gly Gly Leu Val Lys Pro Gly Ser Leu Arg Leu
Ser Cys Ala Ala Ser Gly Phe Thr Phe <u>Ser Ser Phe Ala</u>
<u>Met His</u> Trp Val Arg Gln Ala Pro Gly Lys Gly Leu Glu
Trp Ile Ser <u>Val Ile Asp Thr Arg Gly Ala Thr Tyr Tyr</u>
<u>Ala Asp Ser Val Lys Gly</u> Arg Phe Thr Ile Ser Arg Asp
Asn Ala Lys Asn Ser Leu Tyr Leu Gln Met Asn Ser Leu
Arg Ala Glu Asp Thr Ala Val Tyr Tyr Cys Ala Arg <u>Leu</u>
<u>Gly Asn Phe Tyr Tyr Gly Met Asp Val</u> Trp Gly Gln Gly
Thr Thr Val Thr Val Ser Ser

See international application publication no. WO2003/100008 which is incorporated herein by reference in its entirety.

2C6 heavy chain
(SEQ ID NO: 13)
<u>MELGLSWIFLLAILKGVQC</u>

EVQLVESGGGLVQPGRSLRLSCAASGFTFDDYAMHWVRQAPGKGLEVSGI
SWNSGSKGYVDSVKGRFTISRDNAKNSLYLQMNSLRAEDTALYYCAKDIR
IGVAASYYFGMDVWGHGTTVTVSS (SEQ ID NO: 14)
2C6 CDR-H1: GFTFDDYAMH (SEQ ID NO: 15)
2C6 CDR-H2: GISWNSGSKGYVDSVKG (SEQ ID NO: 16)
2C6 CDR-H3: DIRIGVAASYYFGMDV

2C6 Light chain
(SEQ ID NO: 17)
<u>MDMRVPAQLLGLLLLWLPGARC</u>

AIQLTQSPSSLSASVGDRVTITCRASQGISSVLAWYQQKPGKAPKLLIYD
ASSLESGVPSRFSGSGSGTDFTLTISSLQPEDFATYYCQQFNSYPYTFGQ
GTKLEIK (SEQ ID NO: 18)
2C6 CDR-L1: RASQGISSVLA (SEQ ID NO: 19)
2C6 CDR-L2: DASSLES (SEQ ID NO: 20)
2C6 CDR-L3: QQFNSYPYT

9H2 Heavy chain
(SEQ ID NO: 21)
<u>MDWTWRILFLVAAATGAHS</u>

QVQLVQSGAEVKKPGASVKVSCKASGYTFTSYVMHWVRQAPGQRLEWMGW
INAGNGNTKYSQKFQGRVTITRDTSASTVYMELSSLRSEDTAVYYCARGG
MPVAGPGYFYYYGMDVWGQGTTVTVSS (SEQ ID NO: 22)
9H2 CDR-H1: GYTFTSYVMH (SEQ ID NO: 23)
9H2 CDR-H2: WINAGNGNTKYSQKFQG (SEQ ID NO: 24)
9H2 CDR-H3: GGMPVAGPGYFYYYGMDV

9H2 Light chain
(SEQ ID NO: 25)
<u>METPAQLLFLLLLWLPDTTG</u>

EIVLTQSPGTLSLSPGERATLSCRASQSVSRSYLAWYQQKPGQAPRLLIY
GASSRATGIPDRFSGSGSGTDFTLTISRLEPEDFAVYCCQQYGSSPWTFG
QGTKVEIKRT (SEQ ID NO: 26)
9H2 CDR-L1: RASQSVSRSYLA (SEQ ID NO: 27)
9H2 CDR-L2: GASSRAT (SEQ ID NO: 28)
9H2 CDR-L3: QQYGSSPWT

Heavy chain immunoglobulin variable region # 1.0 sequence
(SEQ ID NO: 29)
E VQLLESGGGL VQPGGSLRLS CTASGFTFSS YAMNWVRQAP
GKGLEVIVSAI SGSGGTTFYA DSVKGRFTIS RDNSRTTLYL
QMNSLRAEDT AVYYCAKDLG WSDSYYYYG MDVWGQGTTV TVSS;

Light chain immunoglobulin variable region # 1.0 sequence
(SEQ ID NO: 30)
DIQMTQFP SSLSASVGDR VTITCRASQG IRNDLGWYQQ
KPGKAPKRLI YAASRLHRGV PSRFSGSGSG TEFTLTISSL
QPEDFATYYC LQHNSYPCSF GQGTKLEIKR;

Embodiments of the invention include those wherein the plasmid includes more than one immunoglobulin, for example, a combination of any of those set forth herein (e.g., heavy chain lg. #1.0 and light chain lg. #1.0; or LCC and HCA; or LCF and HCA; or LCC and HCB).

Protein Expression and Purification

A further aspect of the present invention relates to a method for the production of a recombinant protein (e.g., anti-TGFβ, anti-IGF1R, anti-IL-23, anti-EGFR, anti-IL-17, anti-PD1, anti-IL-1, anti-HGF), comprising the steps of: a) transfecting a host cell or host cell line (e.g., a mammalian host cell or host cell line) with an expression vector according to the invention; b) culturing the cell under appropriate conditions to enable growth and/or propagation of the cell and expression/production of the recombinant protein; and, optionally c) harvesting the recombinant protein produced. Methods for harvesting (isolating and/or purifying) a given protein from, e.g., a cell, a cell culture or the medium in which cells have been cultured are well known in the art. By way of nonlimiting example, proteins can be isolated and/or purified from biological material by salt or alcohol precipitation (e.g., ammonium sulfate precipitation or ethanol precipitation), affinity chromatography (e.g., used in conjunction with a purification tag); fractionation on immunoaffinity or ion-exchange columns; high pressure liquid chromatography (HPLC); reversed-phase HPLC; chromatography on silica or on a cation-exchange resin such as DEAE; chromatofocusing;); isoelectric focusing; countercurrent distribution; SDS-PAGE; gel filtration (using, e.g., Sephadex G-75); and protein A Sepharose columns to remove contaminants such as IgG. Such purification methods are well known in the art and are disclosed, e.g., in "*Guide to Protein Purification*", Methods in Enzymology, Vol. 182, M. Deutscher, Ed., 1990, Academic Press, New York, N.Y.

Growth of mammalian cells in liquid aqueous culture is well known in the art. Examples of mammalian cell culture growth media which are known in the art include EX-CELL ACF, CHO medium (Sigma-Aldrich (St. Louis, Mo.); discussed further below), DMEM, DMEM/F-12, F-10 Nutrient Mixture, RPMI Medium 1640, F-12 Nutrient Mixture, Medium 199, Eagle's MEM, RPMI, 293 media, and Iscove's Media.

Cell growth can be performed in any of several systems. For example, cell growth can be done in a simple flask, e.g., a glass shake flask. Other systems include tank bioreactors, bag bioreactors and disposable bioreactors. A tank bioreactor includes, typically, a metal vessel (e.g., a stainless steel jacketed vessel) in which cells are growth in a liquid medium. Tank bioreactors can be used for a wide range of culture volumes (e.g., 100 l, 150 l, 10000 l, 15000 l). Tank bioreactors often have additional features for controlling cell growth conditions, including means for temperature control, medium agitation, controlling sparge gas concentrations, controlling pH, controlling $O_2$ concentration, removing samples from the medium, reactor weight indication and control, cleaning hardware, sterilizing the hardware, piping or tubing to deliver all services, adding media, control pH, control solutions, and control gases, pumping sterile fluids into the growth vessel and, supervisory control and a data acquisition. Classifications of tank bioreactor include stirred tank reactors wherein mechanical stirrers (e.g., impellers) are used to mix the reactor to distribute heat and materials (such as oxygen and substrates). Bubble column reactors are tall reactors which use air alone to mix the contents. Air lift reactors are similar to bubble column reactors, but differ by the fact that they contain a draft tube. The draft tube is typically an inner tube which improves circulation and oxygen transfer and equalizes shear forces in the reactor. In fluidized bed reactors, cells are "immobilized" on small particles which move with the fluid. The small particles create a large surface area for cells to stick to and enable a high rate of transfer of oxygen and nutrients to the cells. In packed bed reactors cells are immobilized on large particles. These particles do not move with the liquid. Packed bed reactors are simple to construct and operate but can suffer from blockages and from poor oxygen transfer. A disposable bioreactor is a disposable, one-time use bioreactor. Often, disposable bioreactors possess features similar to non-disposable bioreactors (e.g., agitation system, sparge, probes, ports, etc.).

Particularly where a polypeptide is isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

In some embodiments, the protein of interest is with a second polypeptide or polynucleotide moiety, which may be referred to as a "tag" or "marker". A tag may be used, for example, to facilitate purification or detection of the polypeptide after expression. A fused polypeptide may be constructed, for example, by in-frame insertion of a polynucleotide encoding the tag on the 5' or 3' end of the polynucleotide encoding the polypeptide to be expressed. The fused polynucleotide may then be expressed in the expression system of the invention. Such tags include glutathione-S-transferase (GST), hexahistidine (His6) tags, maltose binding protein (MBP) tags, hemagglutinin (HA) tags, cellulose binding protein (CBP) tags and myc tags. Detectable tags such as $^{32}P$, $^{35}S$, $^{3}H$, $^{99m}TC$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

One skilled in the art appreciates that purification methods suitable for the polypeptide of interest may require modification to account for changes in the character of the polypeptide upon expression in recombinant cell culture.

Kits

The vectors of the invention may be provided in a kit. The kits of the invention may include, in addition to one or more vectors, any reagent which may be employed in the use of the vector. In one embodiment, the kit includes reagents necessary for transformation of the vectors into mammalian cells. For example, the kit may include reagents for a calcium phosphate transformation procedure: calcium chloride, buffer (e.g., 2× HEPES buffered saline), and sterile, distilled water. In another embodiment, the kit includes reagents for a DEAE-Dextran transformation: Chloroquine in PBS, DEAE-dextran in PBS and Phosphate buffered saline. In yet another embodiment, reagents for a liposome transformation are included in the kit: Liposomes extruded from DOTAP/cholesterol extruded liposomes. For example, the kit may include the cationic lipid-based transfection reagent Lipofectamine™ (Invitrogen Life Technologies; Carlsbad, Calif.).

The kit may include reagents required for bacterial transformation of the vectors of the invention. For example, the kit may include transformation competent bacteria (e.g., DH1, DH5, DH5α, XL1-Blue, SURE, SCS110, OneShot Top 10, or HB101).

The kit may include growth media or reagents required for making growth media. For example, in one embodiment, the kit can include fetal calf serum or DMEM (Dulbecco/Vogt modified Eagle's (Harry Eagle) minimal essential medium) for growth of mammalian cells. In another embodiment, the kit can contain powdered Luria broth media or Luria broth plates containing an appropriate antibiotic (e.g., ampicillin or kanamycin) for growing bacteria.

Components supplied in the kit may be provided in appropriate vials or containers (e.g., plastic or glass vials). The kit can include appropriate label directions for storage, and appropriate instructions for usage.

EXAMPLE

The following example is provided to further describe the present invention and should not be construed as a limitation thereof. The scope of the present invention includes any and all of the methods which are set forth below in the following example.

Example 1

Construction of pUHAB

The multiple cloning site of pUHAB, as shown in SEQ ID NO: 2, was synthesized using PCR. The PCR product and the vector of SEQ ID NO: 3 (Vector A; see FIG. 3) were digested by the restriction enzymes AflII and BamHI. The digested PCR product was then ligated to the digested Vector A to form the pUHAB vector (SEQ ID NO: 1). pUHAB was transformed into cells, which were positively selected for presence of the vector. Finally, the integrity of the pUHAB multiple cloning site was confirmed by sequencing.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

I claim:

1. A method for producing a recombinant polypeptide in an isolated host cell, comprising introducing a polynucleotide encoding the polypeptide into a multiple cloning site of a vector, wherein the vector comprises the nucleotide sequence set forth in SEQ ID NO: 1, and introducing said vector comprising the polynucleotide encoding the polypeptide into a host cell under conditions which allow for expression of the polypeptide in said cell.

2. The method of claim 1, further comprising purifying the polypeptide.

3. The method of claim 1 wherein the polypeptide comprises an amino acid sequence selected from the group consisting of SEQ ID NOs: 5-30.

4. The method of claim 1 wherein the polypeptide is an immunoglobulin.

* * * * *

SEQUENCE LISTING

```
<160> NUMBER OF SEQ ID NOS: 30

<210> SEQ ID NO 1
<211> LENGTH: 7045
<212> TYPE: DNA
<213> ORGANISM: Artificial Sequence
<220> FEATURE:
<223> OTHER INFORMATION: pUHAB plasmid vector sequecne

<400> SEQUENCE: 1
gctggatcca gatccccctc gctttcttgc tgtccaattt ctattaaagg ttcctttgtt      60
ccctaagtcc aactactaaa ctgggggata ttatgaaggg ccttgagcat ctggattctg     120
cctaataaaa aacatttatt ttcattgcaa tgatgtattt aaattatttc tgaatatttt     180
actaaaaagg gaatgtggga ggtcagtgca tttaaaacat aaagaaatga agaggggggat    240 ctgtcgacaa gctctagaga gctcacgcgt tgatcatgta caggccggcc aagctttcga     300
ctagcttggc acgccagaaa tccgcgcggt ggttttggg ggtcgggggt gtttggcagc      360
cacagacgcc cggtgttcgt gtcgcgccag tacatgcggt ccatgcccag gccatccaaa     420
aaccatgggt ctgtctgctc agtccagtcg tggacctgac cccacgcaac gcccaaaata     480 ataacccca cgaaccataa accattcccc atgggggacc ccgtccctaa cccacggggc      540
cagtggctat ggcagggcct gccgccccga cgttggctgc gagccctggg ccttcacccg     600
aacttggggg gtggggtggg gaaaaggaag aaacgcgggc gtattggccc caatgggggtc    660 tcggtggggt atcgacagag tgccagccct gggaccgaac cccgcgttta tgaacaaacg     720
acccaacacc cgtgcgtttt attctgtctt tttattgccg tcatagcgcg ggttccttcc     780
ggtattgtct ccttccgtgt ttcagttagc ctcccccatc tcccgatccg gacgagtgct     840
ggggcgtcgg tttccactat cggcgagtac ttctacacag ccatcggtcc agacggccgc     900
gcttctgcgg gcgatttgtg tacgcccgac agtcccggct ccggatcgga cgattgcgtc     960
gcatcgaccc tgcgcccaag ctgcatcatc gaaattgccg tcaaccaagc tctgatagag    1020
ttggtcaaga ccaatgcgga gcatatacgc ccggagccgc ggcgatcctg caagctccgg    1080
atgcctccgc tcgaagtagc gcgtctgctg ctccatacaa gccaaccacg gcctccgaaa    1140
gaagatgttg gcgacctcgt attgggaatc cccgaacatc gcctcgctcc agtcaatgac    1200
cgctgttatg cggccattgt ccgtcaggac attgttggag ccgaaatccg cgtgcacgag    1260
gtgccggact tcggggcagt cctcggccca aagcatcagc tcatcgagag cctgcgcgac    1320
ggacgcactg acggtgtcgt ccatcacagt ttgccagtga tacacatggg gatcagcaat    1380
cgcgcatatg aaatcacgcc atgtagtgta ttgaccgatt ccttgcggtc cgaatgggcc    1440
```

```
gaacccgctc gtctggctaa gatcggccgc agcgatcgca tccatggcct ccgcgaccgg    1500
ctgcagaaca gcgggcagtt cggtttcagg caggtcttgc aacgtgacac cctgtgcacg    1560
gcgggagatg caataggtca ggctctcgct gaattcccca atgtcaagca cttccggaat    1620
cgggagcgcg gccgatgcaa agtgccgata aacataacga tctttgtaga aaccatcggc    1680
gcagctattt acccgcagga catatccacg ccctcctaca tcgaagctga aagcacgaga    1740
ttcttcgccc tccgagagct gcatcaggtc ggagacgctg tcgaactttt cgatcagaaa    1800
cttctcgaca gacgtcgcgg tgagttcagg ctttttcata tctcattgcc ccccgggatc    1860
tgcggcacgc tgttgacgct gttaagcggg tcgctgcagg gtcgctcggt gttcgaggcc    1920
acacgcgtca ccttaatatg cgaagtggac ctcggaccgc gccgccccga ctgcatctgc    1980
gtgttcgaat tcgccaatga caagacgctg ggcggggttt gtgtcatcat agaactaaag    2040
acatgcaaat atatttcttc cggggacacc gccagcaaac gcgagcaacg gccacgggg    2100 atgaagcagg gcggcacctc gctaacggat tcaccactcc aagaattgga gccaatcaat    2160
tcttgcggag aactgtgaat gcgcaaacca acccttggca gaacatatcc atcgcgtccg    2220
ccatctccag cagccgcacg cggcgcatct cggggccgac gcgctgggct acgtcttgct    2280
ggcgttcgca caggccggcc agcgcgctca ctggccgtcg ttttacaacg tcgtgactgg    2340
gaaaaccctg gcgttaccca acttaatcgc cttgcagcac atcccccttt cgccagctgg    2400
cgtaatagcg aagaggcccg caccgatcgc ccttcccaac agttgcgcag cctgaatggc    2460
gaatgggacg cgccctgtag cggcgcatta agcgcggcgg gtgtggtggt tacgcgcagc    2520
gtgaccgcta cacttgccag cgccctagcg cccgctcctt tcgctttctt cccttccttt    2580
ctcgccacgt tcgccggctt tccccgtcaa gctctaaatc gggggctccc tttagggttc    2640
cgatttagtg ctttacggca cctcgacccc aaaaaacttg attagggtga tggttcacgt    2700
agtgggccat cgccctgata gacggttttt cgccctttga cgttggagtc acgttctttt    2760
aatagtggac tcttgttcca aactggaaca acactcaacc ctatctcggt ctattctttt    2820
gatttataag ggattttgcc gatttcggcc tattggttaa aaaatgagct gatttaacaa    2880
aaatttaacg cgaattttaa caaaatatta acgcttacaa tttaggtggc acttttcggg    2940
gaaatgtgcg cggaacccct atttgtttat ttttctaaat acattcaaat atgtatccgc    3000
tcatgagaca ataaccctga taaatgcttc aataatattg aaaaggaag agtatgagta    3060 ttcaacattt ccgtgtcgcc cttattccct tttttgcggc attttgcctt cctgtttttg    3120
ctcacccaga aacgctggtg aaagtaaaag atgctgaaga tcagttgggt gcacgagtgg    3180
gttacatcga actggatctc aacagcggta agatccttga gttttcgc cccgaagaac    3240 gcctgaatcg ccccatcatc cagccagaaa gtgagggagc cacggttgat gagagctttg    3300
ttgtaggtgg accagttggt gattttgaac ttttgctttg ccacggaacg gtctgcgttg    3360
tcgggaagat gcgtgatctg atccttcaac tcagcaaaag ttcgatttat caacaaagc    3420 cacgttgtgt ctcaaaatct ctgatgttac attgcacaag ataaaaatat atcatcatga    3480
acaataaaac tgtctgctta cataaacagt aatacaaggg gtgttatgag ccatattcaa    3540
cgggaaacgt cttgctcgag gccgcgatta aattccaaca tggatgctga tttatatggg    3600
tataaatggg ctcgcgataa tgtcgggcaa tcaggtgcga caatctatcg attgtatggg    3660
aagcccgatg cgccagagtt gtttctgaaa catggcaaag gtagcgttgc caatgatgtt    3720
acagatgaga tggtcagact aaactggctg acggaattta tgcctcttcc gaccatcaag    3780
cattttatcc gtactcctga tgatgcatgg ttactcacca ctgcgatccc cgggaaaaca    3840
```

```
gcattccagg tattagaaga atatcctgat tcaggtgaaa atattgttga tgcgctggca    3900
gtgttcctgc gccggttgca ttcgattcct gtttgtaatt gtccttttaa cagcgatcgc    3960
gtatttcgtc tcgctcaggc gcaatcacga atgaataacg gtttggttga tgcgagtgat    4020
tttgatgacg agcgtaatgg ctggcctgtt gaacaagtct ggaaagaaat gcataagctt    4080
ttgccattct caccggattc agtcgtcact catggtgatt tctcacttga taaccttatt    4140
tttgacgagg ggaaattaat aggttgtatt gatgttggac gagtcggaat cgcagaccga    4200
taccaggatc ttgccatcct atggaactgc ctcggtgagt tttctccttc attacagaaa    4260
cggcttttc aaaaatatgg tattgataat cctgatatga ataaattgca gtttcatttg     4320
atgctcgatg agttttcta atcagaattg gttaattggt tgtaacactg gcagagcatt     4380
acgctgactt gacgggacgg cggctttgtt gaataaatcg aacttttgct gagttgaagg    4440
atcagatcac gcatcttccc gacaacgcag accgttccgt ggcaaagcaa aagttcaaaa    4500
tcaccaactg gtccacctac aacaaagctc tcatcaaccg tggctccctc actttctggc    4560
tggatgatgg ggcgattcag gcgttgcgca aactattaac tggcgaacta cttactctag    4620
cttcccggca acaattaata gactggatgg aggcggataa agttgcagga ccacttctgc    4680
gctcggccct tccggctggc tggtttattg ctgataaatc tggagccggt gagcgtgggt    4740
ctcgcggtat cattgcagca ctggggccag atggtaagcc ctcccgtatc gtagttatct    4800
acacgacggg gagtcaggca actatggatg aacgaaatag acagatcgct gagataggtg    4860
cctcactgat taagcattgg taactgtcag accaagttta ctcatatata ctttagattg    4920
atttaaaact tcatttttaa tttaaaagga tctaggtgaa gatcctttt gataatctca     4980
tgaccaaaat cccttaacgt gagttttcgt tccactgagc gtcagacccc gtagaaaaga    5040
tcaaaggatc ttcttgagat cctttttttc tgcgcgtaat ctgctgcttg caaacaaaaa    5100
aaccaccgct accagcggtg gtttgtttgc cggatcaaga gctaccaact ctttttccga    5160
aggtaactgg cttcagcaga gcgcagatac caaatactgt ccttctagtg tagccgtagt    5220
taggccacca cttcaagaac tctgtagcac cgcctacata cctcgctctg ctaatcctgt    5280
taccagtggc tgctgccagt ggcgataagt cgtgtcttac cgggttggac tcaagacgat    5340
agttaccgga taaggcgcag cggtcgggct gaacggggg ttcgtgcaca cagcccagct     5400
tggagcgaac gacctacacc gaactgagat acctacagcg tgagctatga aaagcgcca     5460
cgcttcccga agggagaaag gcggacaggt atccggtaag cggcagggtc ggaacaggag    5520
agcgcacagg ggagcttcca gggggaaacg cctggtatct ttatagtcct gtcgggtttc    5580
gccacctctg acttgagcgt cgatttttgt gatgctcgtc aggggggcgg agcctatgga    5640
aaaacgccag caacgcggcc ttttacggtt cctggccttt tgctggcctt tttgctcaca    5700
tgttctttcc tgcgttatcc cctgattctg tggataaccg tattaccgcc tttgagtgag    5760
ctgataccgc tcgccgcagc cgaacgaccg agcgcagcga gtcagtgagc gaggaagcgg    5820
aagagcgccc aatacgcaaa ccgcctctcc ccgcgcgttg gccgattcat taatgcagct    5880
ggcacgacag gtttcccgac tggaaagcgg gcagtgagcg caacgcaatt aatgtgagtt    5940
agctcactca ttaggcaccc caggctttac actttatgct tccggctcgt atgttgtgtg    6000
gaattgtgag cggataacaa tttcacacag gaaacagcta tgaccatgat tacgccaagc    6060
gcgccgttta aaccctcagc taccgatgta cgggccagat atacgcgttg acattgatta    6120
ttgactagtt attaatagta atcaattacg gggtcattag ttcatagccc atatatggag    6180
ttccgcgtta cataacttac ggtaaatggc ccgcctggct gaccgcccaa cgacccccgc    6240
```

-continued

```
ccattgacgt caataatgac gtatgttccc atagtaacgc caatagggac tttccattga      6300
cgtcaatggg tggactattt acggtaaact gcccacttgg cagtacatca agtgtatcat      6360
atgccaagta cgccccctat tgacgtcaat gacggtaaat ggcccgcctg cattatgcc       6420 cagtacatga ccttatggga cttccctact tggcagtaca tctacgtatt agtcatcgct      6480
attaccatgg tgatgcggtt ttggcagtac atcaatgggc gtggatagcg gtttgactca      6540
cggggatttc caagtctcca ccccattgac gtcaatggga gtttgttttg gcaccaaaat      6600
caacgggact ttccaaaatg tcgtaacaac tccgccccat tgacgcaaat gggcggtagg      6660
cgtgtacggt gggaggtcta taagcaga gctctctggc taactagaga acccactgct        6720
tactggctta tcgaaattaa tacgactcac tatagcaatt gcacgtgtgg ccacaggtaa      6780
gtttaaagct caggtcgaga ccgggccttt gtccggcgct cccttggagc ctacctagac      6840
tcagccggct ctccacgctt tgcctgaccc tgcttgctca actctacgtc tttgtttcgt      6900
tttctgttcc tttctctcca caggcttaag agtgttaacg cgacctaggt aagatatcct      6960
tggtaccgtg ttaattaact ggcggccgct gtgtatacgt ggcccgggct gggggcccat      7020
agctagcgtt agatctctgg catgc                                            7045

<210> SEQ ID NO 2
<211> LENGTH: 130
<212> TYPE: DNA
<213> ORGANISM: Artificial Sequence
<220> FEATURE:
<223> OTHER INFORMATION: pUHAB multiple cloning site

<400> SEQUENCE: 2
cttaagagtg ttaacgcgac ctaggtaaga tatccttggt accgtgttaa ttaactggcg       60
gccgctgtgt atacgtggcc cgggctgggg gcccatagct agcgttagat ctctggcatg      120
cgctggatcc                                                             130

<210> SEQ ID NO 3
<211> LENGTH: 8391
<212> TYPE: DNA
<213> ORGANISM: Artificial Sequence
<220> FEATURE:
<223> OTHER INFORMATION: vector A sequence

<400> SEQUENCE: 3
ttaagcctgt ggagagaaag gaacagaaaa cgaaacaaag acgtagagtt gagcaagcag       60
ggtcaggcaa agcgtggaga gccggctgag tctaggtagg ctccaaggga gcgccggaca      120
aaggcccggt ctcgacctga gctttaaact tacctgtggc cacacgtgca attgctatag      180
tgagtcgtat taatttcgat aagccagtaa gcagtgggtt ctctagttag ccagagagct      240
ctgcttatat agacctccca ccgtacacgc ctaccgccca tttgcgtcaa tggggcggag      300
ttgttacgac attttggaaa gtcccgttga ttttggtgcc aaaacaaact cccattgacg      360
tcaatggggt ggagacttgg aaatccccgt gagtcaaacc gctatccacg cccattgatg      420
tactgccaaa accgcatcac catggtaata gcgatgacta atacgtagat gtactgccaa      480
gtaggaaagt cccataaggt catgtactgg gcataatgcc aggcgggcca tttaccgtca      540
ttgacgtcaa taggggcgt acttggcata tgatacactt gatgtactgc caagtgggca      600
gtttaccgta aatactccac ccattgacgt caatggaaag tccctattgg cgttactatg      660
ggaacatacg tcattattga cgtcaatggg cggggtcgt tggcggtca gccaggcggg      720 ccatttaccg taagttatgt aacgcggaac tccatatatg gctatgaac taatgacccc      780
```

```
gtaattgatt actattaata actagtcaat aatcaatgtc aacgcgtata tctggcccgt    840
acatcggtag ctgagggttt aaacggcgcg cttggcgtaa tcatggtcat agctgtttcc    900
tgtgtgaaat tgttatccgc tcacaattcc acacaacata cgagccggaa gcataaagtg    960
taaagcctgg ggtgcctaat gagtgagcta actcacatta attgcgttgc gctcactgcc   1020
cgcttttcag tcgggaaacc tgtcgtgcca gctgcattaa tgaatcggcc aacgcgcggg   1080
gagaggcggt ttgcgtattg ggcgctcttc cgcttcctcg ctcactgact cgctgcgctc   1140
ggtcgttcgg ctgcggcgag cggtatcagc tcactcaaag gcggtaatac ggttatccac   1200
agaatcaggg gataacgcag gaaagaacat gtgagcaaaa ggccagcaaa aggccaggaa   1260
ccgtaaaaag gccgcgttgc tggcgttttt ccataggctc cgcccccctg acgagcatca   1320
caaaaatcga cgctcaagtc agaggtggcg aaacccgaca ggactataaa gataccaggc   1380
gtttccccct ggaagctccc tcgtgcgctc tcctgttccg accctgccgc ttaccggata   1440
cctgtccgcc tttctccctt cgggaagcgt ggcgctttct catagctcac gctgtaggta   1500
tctcagttcg gtgtaggtcg ttcgctccaa gctgggctgt gtgcacgaac cccccgttca   1560
gcccgaccgc tgcgccttat ccggtaacta tcgtcttgag tccaacccgg taagacacga   1620
cttatcgcca ctggcagcag ccactggtaa caggattagc agagcgaggt atgtaggcgg   1680
tgctacagag ttcttgaagt ggtggcctaa ctacggctac actagaagga cagtatttgg   1740
tatctgcgct ctgctgaagc cagttacctt cggaaaaaga gttggtagct cttgatccgg   1800
caaacaaacc accgctggta gcggtggttt ttttgtttgc aagcagcaga ttacgcgcag   1860
aaaaaaagga tctcaagaag atcctttgat cttttctacg gggtctgacg ctcagtggaa   1920
cgaaaactca cgttaaggga ttttggtcat gagattatca aaaaggatct tcacctagat   1980
ccttttaaat taaaaatgaa gttttaaatc aatctaaagt atatatgagt aaacttggtc   2040
tgacagttac caatgcttaa tcagtgaggc acctatctca gcgatctgtc tatttcgttc   2100
atccatagtt gcctgactcc ccgtcgtgta gataactacg atacgggagg gcttaccatc   2160
tggccccagt gctgcaatga taccgcgaga cccacgctca ccggctccag atttatcagc   2220
aataaaccag ccagccggaa gggccgagcg cagaagtggt cctgcaactt tatccgcctc   2280
catccagtct attaattgtt gccgggaagc tagagtaagt agttcgccag ttaatagttt   2340
gcgcaacgcc tgaatcgccc catcatccag ccagaaagtg agggagccac ggttgatgag   2400
agctttgttg taggtggacc agttggtgat tttgaacttt tgctttgcca cggaacggtc   2460
tgcgttgtcg ggaagatgcg tgatctgatc cttcaactcg caaaagttc gatttattca    2520 acaaagccgc cgtcccgtca gtcagcgta atgctctgcc agtgttacaa ccaattaacc   2580
aattctgatt agaaaaactc atcgagcatc aaatgaaact gcaatttatt catatcagga   2640
ttatcaatac catattttg aaaaagccgt ttctgtaatg aaggagaaaa ctcaccgagg    2700
cagttccata ggatgcaag atcctggtat cggtctgcga ttccgactcg tccaacatca    2760
atacaaccta ttaatttccc ctcgtcaaaa ataaggttat caagtgagaa atcaccatga   2820
gtgacgactg aatccggtga gaatggcaaa agcttatgca tttctttcca gacttgttca   2880
acaggccagc cattacgctc gtcatcaaaa tcactcgcat caaccaaacc gttattcatt   2940
cgtgattgcg cctgagcgag acgaaatacg cgatcgctgt taaaaggaca attacaaaca   3000
ggaatcgaat gcaaccggcg caggaacact gccagcgcat caacaatatt ttcacctgaa   3060
tcaggatatt cttctaatac ctggaatgct gttttcccgg ggatcgcagt ggtgagtaac   3120
catgcatcat caggagtacg gataaaatgc ttgatggtcg aagaggcat aaattccgtc    3180
```

```
agccagttta gtctgaccat ctcatctgta acatcattgg caacgctacc tttgccatgt    3240
ttcagaaaca actctggcgc atcgggcttc ccatacaatc gatagattgt cgcacctgat    3300
tgcccgacat tatcgcgagc ccatttatac ccatataaat cagcatccat gttggaattt    3360
aatcgcggcc tcgagcaaga cgtttcccgt tgaatatggc tcataacacc ccttgtatta    3420
ctgtttatgt aagcagacag ttttattgtt catgatgata tattttttatc ttgtgcaatg    3480 taacatcaga gattttgaga cacaacgtgg ctttgttgaa taaatcgaac ttttgctgag    3540
ttgaaggatc agatcacgca tcttcccgac aacgcagacc gttccgtggc aaagcaaaag    3600
ttcaaaatca ccaactggtc cacctacaac aaagctctca tcaaccgtgg ctccctcact    3660
ttctggctgg atgatggggc gattcaggcg ttcttcgggg cgaaaactct caaggatctt    3720
accgctgttg agatccagtt cgatgtaacc cactcgtgca cccaactgat cttcagcatc    3780
ttttactttc accagcgttt ctgggtgagc aaaaacagga aggcaaaatg ccgcaaaaaa    3840
gggaataagg gcgacacgga aatgttgaat actcatactc ttccttttc aatattattg     3900 aagcatttat cagggttatt gtctcatgag cggatacata tttgaatgta tttagaaaaa    3960
taaacaaata ggggttccgc gcacatttcc ccgaaaagtg ccacctaaat tgtaagcgtt    4020
aatattttgt taaaattcgc gttaaatttt tgttaaatca gctcatttt taaccaatag     4080 gccgaaatcg gcaaaatccc ttataaatca aagaataga ccgagatagg gttgagtgtt     4140
gttccagttt ggaacaagag tccactatta agaacgtgg actccaacgt caagggcga      4200 aaaccgtct atcagggcga tggcccacta cgtgaaccat caccctaatc aagttttttg      4260
gggtcgaggt gccgtaaagc actaaatcgg aaccctaaag ggagccccg atttagagct      4320 tgacggggaa agccggcgaa cgtggcgaga aggaaggga agaaagcgaa aggagcgggc      4380
gctagggcgc tggcaagtgt agcggtcacg ctgcgcgtaa ccaccacacc cgccgcgctt    4440
aatgcgccgc tacagggcgc gtcccattcg ccattcaggc tgcgcaactg ttgggaaggg    4500
cgatcggtgc gggcctcttc gctattacgc cagctggcga aaggggatg tgctgcaagg     4560 cgattaagtt gggtaacgcc agggttttcc cagtcacgac gttgtaaaac gacggccagt    4620
gagcgcgctg gccggcctgt gcgaacgcca gcaagacgta gcccagcgcg tcggccccga    4680
gatgcgccgc gtgcggctgc tggagatggc ggacgcgatg gatatgttct gccaagggtt    4740
ggtttgcgca ttcacagttc tccgcaagaa ttgattggct ccaattcttg gagtggtgaa    4800
tccgttagcg aggtgccgcc ctgcttcatc cccgtggccc gttgctcgcg tttgctggcg    4860
gtgtccccgg aagaaatata tttgcatgtc tttagttcta tgatgacaca aaccccgccc    4920
agcgtcttgt cattggcgaa ttcgaacacg cagatgcagt cggggcggcg cggtccgagg    4980
tccacttcgc atattaaggt gacgcgtgtg gcctcgaaca ccgagcgacc ctgcagcgac    5040
ccgcttaaca gcgtcaacag cgtgccgcag atcccggggg gcaatgagat atgaaaaagc    5100
ctgaactcac cgcgacgtct gtcgagaagt ttctgatcga aaagttcgac agcgtctccg    5160
acctgatgca gctctcggag ggcgaagaat ctcgtgcttt cagcttcgat gtaggagggc    5220
gtggatatgt cctgcgggta aatagctgcg ccgatggttt ctacaaagat cgttatgttt    5280
atcggcactt tgcatcggcc gcgctcccga ttccggaagt gcttgacatt ggggaattca    5340
gcgagagcct gacctattgc atctcccgcc gtgcacaggg tgtcacgttg caagacctgc    5400
ctgaaaccga actgcccgct gttctgcagc cggtcgcgga ggccatggat gcgatcgctg    5460
cggccgatct tagccagacg agcgggttcg gcccattcgg accgcaagga atcggtcaat    5520
acactacatg gcgtgatttc atatgcgcga ttgctgatcc ccatgtgtat cactggcaaa    5580
```

```
ctgtgatgga cgacaccgtc agtgcgtccg tcgcgcaggc tctcgatgag ctgatgcttt      5640
gggccgagga ctgccccgaa gtccggcacc tcgtgcacgc ggatttcggc tccaacaatg      5700
tcctgacgga caatggccgc ataacagcgg tcattgactg gagcgaggcg atgttcgggg      5760
attcccaata cgaggtcgcc aacatcttct tctggaggcc gtggttggct tgtatggagc      5820
agcagacgcg ctacttcgag cggaggcatc cggagcttgc aggatcgccg cggctccggg      5880
cgtatatgct ccgcattggt cttgaccaac tctatcagag cttggttgac ggcaatttcg      5940
atgatgcagc ttgggcgcag ggtcgatgcg acgcaatcgt ccgatccgga gccgggactg      6000
tcgggcgtac acaaatcgcc cgcagaagcg cggccgtctg gaccgatggc tgtgtagaag      6060
tactcgccga tagtggaaac cgacgcccca gcactcgtcc ggatcgggag atggggagg       6120 ctaactgaaa cacggaagga gacaataccg gaaggaaccc gcgctatgac ggcaataaaa      6180
agacagaata aaacgcacgg gtgttgggtc gtttgttcat aaacgcgggg ttcggtccca      6240
gggctggcac tctgtcgata cccaccgag accccattgg ggccaatacg cccgcgtttc       6300
ttccttttcc ccaccccacc cccaagttc gggtgaaggc ccagggctcg cagccaacgt       6360
cggggcggca ggccctgcca tagccactgg ccccgtgggt tagggacggg gtcccccatg      6420
gggaatggtt tatggttcgt gggggttatt attttgggcg ttgcgtgggg tcaggtccac      6480
gactggactg agcagacaga cccatggttt ttggatggcc tgggcatgga ccgcatgtac      6540
tggcgcgaca cgaacaccgg gcgtctgtgg ctgccaaaca cccccgaccc ccaaaaacca      6600
ccgcgcggat ttctggcgtg ccaagctagt cgaaagcttg gccggcctgt acatgatcaa      6660
cgcgtgagct ctctagagct tgtcgacaga tccccctctt catttcttta tgttttaaat      6720
gcactgacct cccacattcc cttttttagta aaatattcag aaataattta aatacatcat      6780
tgcaatgaaa ataaatgttt tttattaggc agaatccaga tgctcaaggc ccttcataat      6840
atcccccagt ttagtagttg gacttaggga acaaaggaac cttaataga aattggacag       6900 caagaaagcg aggggatct ggatcctccg gacccgtatc tagaatcatc gattcattta       6960
cccggagaca gggagaggct cttctgcgtg tagtggttgt gcagagcctc atgcatcacg      7020
gagcatgaga agacgttccc ctgctgccac ctgctcttgt ccacggtgag cttgctgtag      7080
aggaagaagg agccgtcgga gtccagcacg ggaggcgtgg tcttgtagtt gttctccggc      7140
tgcccattgc tctcccactc cacgcgatg tcgctgggat agaagccttt gaccaggcag       7200
gtcaggctga cctggttctt ggtcagctca tcccgggatg ggggcagggt gtacacctgt      7260
ggttctcggg gctgcccttt ggctttggag atggttttct cgatggggc tgggagggct       7320 ttgttggaga ccttgcactt gtactccttg ccattcagcc agtcctggtg caggacggtg      7380
aggacgctga ccacacggta cgtgctgttg tactgctcct cccgcggctt tgtcttggca      7440
ttatgcacct ccacgccgtc cacgtaccag ttgaacttga cctcagggtc ttcgtggctc      7500
acgtccacca cccacgcatgt gacctcaggg gtccggagaa tcatgagggt gtccttgggt      7560 tttggggga agaggaagac tgacggtccc cccaggagtt caggtgctgg cacggtggg       7620 catgtgtgag ttttgtcaca agatttgggc tcaactttct tgtccacctt ggtgttgctg      7680
ggcttgtgat tcacgttgca gatgtaggtc tgggtgccca agctgctgga gggcacggtc      7740
accacgctgc tgagggagta gagtcctgag gactgtagga cagccgggaa ggtgtgcacg      7800
ccgctggtca gggcgcctga gttccacgac accgtcaccg gttcggggaa gtagtccttg      7860
accaggcagc ccagggccgc tgtgccccca gaggtgctct tggaggaggg tgccagggggg     7920 aagaccgatg ggcccttggt gctagcggag ctcacggtca ccagggtgcc ctgtccccag      7980
```

```
gcatccatga agtagttctc gtaatagtag tcggtgatgt atgcatttct ggcacagtaa        8040
tacacagcgg tgtcggcagc ggtcacgctg ctcagcttca ggctgaactg gttcttggag        8100
gtgtccacgg agatggtcac gcggctcttg aaggcgctgt tatagtcagt gccgccttga        8160
ttccaaatga tgccgatcca ctccagtccc ttgcctggag gctgtctgat ccagctcacg        8220
ctgtggctgg gcaggctgaa tccagacacg gtacaggtca ggctcagggt ctcgctaggc        8280
ttcaccaggc ctggtccaga ctcctgcagc tgcacctggg acagcacaca gcttgggaat        8340
gtcaccaggc agaacagcag ccccagcaca gccatggtgg cggcagtact c                 8391
```

<210> SEQ ID NO 4
<211> LENGTH: 152
<212> TYPE: DNA
<213> ORGANISM: Artificial Sequence
<220> FEATURE:
<223> OTHER INFORMATION: intron

<400> SEQUENCE: 4

```
caggtaagtt taaagctcag gtcgagaccg ggcctttgtc cggcgctccc ttggagccta          60
cctagactca gccggctctc cacgctttgc ctgaccctgc ttgctcaact ctacgtcttt         120
gtttcgtttt ctgttccttt ctctccacag gc                                      152
```

<210> SEQ ID NO 5
<211> LENGTH: 128
<212> TYPE: PRT
<213> ORGANISM: Homo sapiens

<400> SEQUENCE: 5

```
Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125
```

<210> SEQ ID NO 6
<211> LENGTH: 137
<212> TYPE: PRT
<213> ORGANISM: Homo sapiens

<400> SEQUENCE: 6

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
```

```
                    50                  55                  60
Glu Trp Ile Ser Val Ile Asp Thr Arg Gly Ala Thr Tyr Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
            115                 120                 125

Gln Gly Thr Thr Val Thr Val Ser Ser
            130                 135

<210> SEQ ID NO 7
<211> LENGTH: 128
<212> TYPE: PRT
<213> ORGANISM: Homo sapiens

<400> SEQUENCE: 7

Met Ser Pro Ser Gln Leu Ile Gly Phe Leu Leu Leu Trp Val Pro Ala
 1               5                  10                  15

Ser Arg Gly Glu Ile Val Leu Thr Gln Ser Pro Asp Ser Leu Ser Val
             20                  25                  30

Thr Pro Gly Glu Arg Val Thr Ile Thr Cys Arg Ala Ser Gln Ser Ile
         35                  40                  45

Gly Ser Ser Leu His Trp Tyr Gln Gln Lys Pro Gly Gln Ser Pro Lys
     50                  55                  60

Leu Leu Ile Lys Tyr Ala Ser Gln Ser Leu Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
            115                 120                 125

<210> SEQ ID NO 8
<211> LENGTH: 128
<212> TYPE: PRT
<213> ORGANISM: Homo sapiens

<400> SEQUENCE: 8

Met Ser Pro Ser Gln Leu Ile Gly Phe Leu Leu Leu Trp Val Pro Ala
 1               5                  10                  15

Ser Arg Gly Glu Ile Val Leu Thr Gln Ser Pro Asp Ser Leu Ser Val
             20                  25                  30

Thr Pro Gly Glu Arg Val Thr Ile Thr Cys Arg Ala Ser Gln Ser Ile
         35                  40                  45

Gly Ser Ser Leu His Trp Tyr Gln Gln Lys Pro Gly Gln Ser Pro Lys
     50                  55                  60

Leu Leu Ile Lys Tyr Ala Ser Gln Ser Leu Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
            115                 120                 125
```

<210> SEQ ID NO 9
<211> LENGTH: 128
<212> TYPE: PRT
<213> ORGANISM: Homo sapiens

<400> SEQUENCE: 9

Met Ser Pro Ser Gln Leu Ile Gly Phe Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 10
<211> LENGTH: 128
<212> TYPE: PRT
<213> ORGANISM: Homo sapiens

<400> SEQUENCE: 10

Met Ser Pro Ser Gln Leu Ile Gly Phe Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 11
<211> LENGTH: 137
<212> TYPE: PRT
<213> ORGANISM: Homo sapiens

<400> SEQUENCE: 11

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe

```
                35                  40                  45
Ser Ser Phe Ala Met His Trp Val Arg Gln Ala Pro Gly Lys Gly Leu
     50                  55                  60

Glu Trp Ile Ser Val Ile Asp Thr Arg Gly Ala Thr Tyr Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 12
<211> LENGTH: 137
<212> TYPE: PRT
<213> ORGANISM: Homo sapiens

<400> SEQUENCE: 12

Met Glu Phe Gly Leu Ser Trp Val Phe Leu Val Ala Ile Leu Lys Gly
 1               5                  10                  15

Val Gln Cys Glu Val Gln Leu Val Gln Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Phe Ala Met His Trp Val Arg Gln Ala Pro Gly Lys Gly Leu
     50                  55                  60

Glu Trp Ile Ser Val Ile Asp Thr Arg Gly Ala Thr Tyr Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 13
<211> LENGTH: 144
<212> TYPE: PRT
<213> ORGANISM: Homo sapiens

<400> SEQUENCE: 13

Met Glu Leu Gly Leu Ser Trp Ile Phe Leu Leu Ala Ile Leu Lys Gly
 1               5                  10                  15

Val Gln Cys Glu Val Gln Leu Val Glu Ser Gly Gly Gly Leu Val Gln
             20                  25                  30

Pro Gly Arg Ser Leu Arg Leu Ser Cys Ala Ala Ser Gly Phe Thr Phe
         35                  40                  45

Asp Asp Tyr Ala Met His Trp Val Arg Gln Ala Pro Gly Lys Gly Leu
     50                  55                  60

Glu Trp Val Ser Gly Ile Ser Trp Asn Ser Gly Ser Lys Gly Tyr Val
 65                  70                  75                  80

Asp Ser Val Lys Gly Arg Phe Thr Ile Ser Arg Asp Asn Ala Lys Asn
                 85                  90                  95
```

Ser Leu Tyr Leu Gln Met Asn Ser Leu Arg Ala Glu Asp Thr Ala Leu
            100                 105                 110

Tyr Tyr Cys Ala Lys Asp Ile Arg Ile Gly Val Ala Ala Ser Tyr Tyr
        115                 120                 125

Phe Gly Met Asp Val Trp Gly His Gly Thr Thr Val Thr Val Ser Ser
        130                 135                 140

<210> SEQ ID NO 14
<211> LENGTH: 10
<212> TYPE: PRT
<213> ORGANISM: Homo sapiens

<400> SEQUENCE: 14

Gly Phe Thr Phe Asp Asp Tyr Ala Met His
1               5                   10

<210> SEQ ID NO 15
<211> LENGTH: 17
<212> TYPE: PRT
<213> ORGANISM: Homo sapiens

<400> SEQUENCE: 15

Gly Ile Ser Trp Asn Ser Gly Ser Lys Gly Tyr Val Asp Ser Val Lys
1               5                   10                  15

Gly

<210> SEQ ID NO 16
<211> LENGTH: 16
<212> TYPE: PRT
<213> ORGANISM: Homo sapiens

<400> SEQUENCE: 16

Asp Ile Arg Ile Gly Val Ala Ala Ser Tyr Tyr Phe Gly Met Asp Val
1               5                   10                  15

<210> SEQ ID NO 17
<211> LENGTH: 129
<212> TYPE: PRT
<213> ORGANISM: Homo sapiens

<400> SEQUENCE: 17

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Val Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Tyr Thr Phe Gly Gln Gly Thr Lys Leu Glu Ile
        115                 120                 125

Lys

```
<210> SEQ ID NO 18
<211> LENGTH: 11
<212> TYPE: PRT
<213> ORGANISM: Homo sapiens

<400> SEQUENCE: 18

Arg Ala Ser Gln Gly Ile Ser Ser Val Leu Ala
1               5                   10

<210> SEQ ID NO 19
<211> LENGTH: 7
<212> TYPE: PRT
<213> ORGANISM: Homo sapiens

<400> SEQUENCE: 19

Asp Ala Ser Ser Leu Glu Ser
1               5

<210> SEQ ID NO 20
<211> LENGTH: 9
<212> TYPE: PRT
<213> ORGANISM: Homo sapiens

<400> SEQUENCE: 20

Gln Gln Phe Asn Ser Tyr Pro Tyr Thr
1               5

<210> SEQ ID NO 21
<211> LENGTH: 146
<212> TYPE: PRT
<213> ORGANISM: Homo sapiens

<400> SEQUENCE: 21

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Val Met His Trp Val Arg Gln Ala Pro Gly Gln Arg Leu
        50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Gly Met Pro Val Ala Gly Pro Gly Tyr Phe
        115                 120                 125

Tyr Tyr Tyr Gly Met Asp Val Trp Gly Gln Gly Thr Thr Val Thr Val
    130                 135                 140

Ser Ser
145

<210> SEQ ID NO 22
<211> LENGTH: 10
<212> TYPE: PRT
<213> ORGANISM: Homo sapiens

<400> SEQUENCE: 22

Gly Tyr Thr Phe Thr Ser Tyr Val Met His
1               5                   10
```

<210> SEQ ID NO 23
<211> LENGTH: 17
<212> TYPE: PRT
<213> ORGANISM: Homo sapiens

<400> SEQUENCE: 23

Trp Ile Asn Ala Gly Asn Gly Asn Thr Lys Tyr Ser Gln Lys Phe Gln
1               5                   10                  15

Gly

<210> SEQ ID NO 24
<211> LENGTH: 18
<212> TYPE: PRT
<213> ORGANISM: Homo sapiens

<400> SEQUENCE: 24

Gly Gly Met Pro Val Ala Gly Pro Gly Tyr Phe Tyr Tyr Tyr Gly Met
1               5                   10                  15

Asp Val

<210> SEQ ID NO 25
<211> LENGTH: 130
<212> TYPE: PRT
<213> ORGANISM: Homo sapiens

<400> SEQUENCE: 25

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Arg Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Cys Cys Gln Gln Tyr
            100                 105                 110

Gly Ser Ser Pro Trp Thr Phe Gly Gln Gly Thr Lys Val Glu Ile Lys
        115                 120                 125

Arg Thr
    130

<210> SEQ ID NO 26
<211> LENGTH: 12
<212> TYPE: PRT
<213> ORGANISM: Homo sapiens

<400> SEQUENCE: 26

Arg Ala Ser Gln Ser Val Ser Arg Ser Tyr Leu Ala
1               5                   10

<210> SEQ ID NO 27
<211> LENGTH: 7
<212> TYPE: PRT
<213> ORGANISM: Homo sapiens

<400> SEQUENCE: 27

```
Gly Ala Ser Ser Arg Ala Thr
1               5

<210> SEQ ID NO 28
<211> LENGTH: 9
<212> TYPE: PRT
<213> ORGANISM: Homo sapiens

<400> SEQUENCE: 28

Gln Gln Tyr Gly Ser Ser Pro Trp Thr
1               5

<210> SEQ ID NO 29
<211> LENGTH: 125
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Tyr Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Trp Ser Asp Ser Tyr Tyr Tyr Tyr Gly Met
            100                 105                 110

Asp Val Trp Gly Gln Gly Thr Thr Val Thr Val Ser Ser
        115                 120                 125

<210> SEQ ID NO 30
<211> LENGTH: 108
<212> TYPE: PRT
<213> ORGANISM: Homo sapiens

<400> SEQUENCE: 30

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg
            100                 105
```